(12) United States Patent
Griffin et al.

(10) Patent No.: US 7,985,594 B2
(45) Date of Patent: Jul. 26, 2011

(54) BIRADICAL POLARIZING AGENTS FOR DYNAMIC NUCLEAR POLARIZATION

(75) Inventors: Robert G. Griffin, Newton, MA (US); Kan-Nian Hu, Silver Spring, MD (US); Timothy M. Swager, Newton, MA (US); Changsik Song, Brighton, MA (US); Eric Dane, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 114 days.

(21) Appl. No.: 12/300,529

(22) PCT Filed: May 10, 2007

(86) PCT No.: PCT/US2007/068659
§ 371 (c)(1),
(2), (4) Date: Apr. 15, 2009

(87) PCT Pub. No.: WO2008/048714
PCT Pub. Date: Apr. 24, 2008

(65) Prior Publication Data
US 2009/0302842 A1     Dec. 10, 2009

Related U.S. Application Data

(60) Provisional application No. 60/747,102, filed on May 12, 2006.

(51) Int. Cl.
*G01N 24/00* (2006.01)
*C07D 471/02* (2006.01)
*C07D 295/24* (2006.01)

(52) U.S. Cl. ........ 436/173; 514/332; 546/116; 546/188; 546/193; 548/519; 548/542

(58) Field of Classification Search .................. 436/173; 514/332; 546/116, 188, 193; 548/519, 542
See application file for complete search history.

(56) References Cited

U.S. PATENT DOCUMENTS
4,521,732 A    6/1985  Pegg et al.
(Continued)

FOREIGN PATENT DOCUMENTS
WO    WO-9639367 A1    12/1996
(Continued)

OTHER PUBLICATIONS

Kopf, P. W. et al, Journal of the American Chemical Society 1970, 92, 4531-4535.*

(Continued)

*Primary Examiner* — Arlen Soderquist
(74) *Attorney, Agent, or Firm* — Choate Hall & Stewart LLP

(57) ABSTRACT

The present invention provides methods for performing dynamic nuclear polarization using biradicals with a structure of formula (I) as described herein. In general, the methods involve (a) providing a frozen sample in a magnetic field, wherein the frozen sample includes a biradical of formula (I) and an analyte with at least one spin half nucleus; (b) polarizing the at least one spin half nucleus of the analyte by irradiating the frozen sample with radiation having a frequency that excites electron spin transitions in the biradical; (c) optionally melting the sample to produce a molten sample; and (d) detecting nuclear spin transitions in the at least one spin half nucleus of the analyte in the frozen or molten sample. The present invention also provides biradicals with a structure of formula (I) with the proviso that $Q_1$ and $Q_2$ are different when $X_1$ and $X_2$ are —O—. The present invention also provides methods for making biradicals with a structure of formula (IA) as described herein.

63 Claims, 12 Drawing Sheets

U.S. PATENT DOCUMENTS

| | | | |
|---|---|---|---|
| 4,682,107 | A | 7/1987 | Bendall et al. |
| 5,085,748 | A | 2/1992 | Yamasaki et al. |
| 5,145,893 | A | 9/1992 | Galbo et al. |
| 5,435,991 | A | 7/1995 | Golman et al. |
| 6,278,893 | B1 | 8/2001 | Ardenkjaer-Larson et al. |
| 6,311,086 | B1 | 10/2001 | Ardenkjaer-Larsen et al. |
| 6,455,542 | B1 | 9/2002 | Anggard et al. |
| 6,515,260 | B1 | 2/2003 | Anderson |
| 7,102,354 | B2 | 9/2006 | Ardenkjaer-Larsen et al. |
| 7,351,402 | B2 | 4/2008 | Griffin et al. |
| 2002/0029586 | A1 | 3/2002 | Driehuys |
| 2002/0058869 | A1 | 5/2002 | Axelsson et al. |
| 2002/0107439 | A1 | 8/2002 | Hersman et al. |
| 2004/0049108 | A1 | 3/2004 | Ardenkjaer-Larsen et al. |

FOREIGN PATENT DOCUMENTS

| | | |
|---|---|---|
| WO | WO-2007134160 A2 | 11/2007 |
| WO | WO-2008048714 A2 | 4/2008 |

OTHER PUBLICATIONS

Luckhurst, G. R. et al, Journal of the American Chemical Society 1970, 92, 4738-4739.*
Chachaty, C. et al, Magnetic Resonance in Chemistry 1995, 33, S174-S177.*
Bosman, A. W. et al, Macromolecules 1997, 30, 3606-3611.*
Martin, R. E. et al, Angewandte Chemie International Edition 1998, 37, 2834-2837.*
Vostrikova K. E. et al, European Journal of Inorganic Chemistry 1999, 1181-1187.*
Afeworki, M.; McKay, R. A.; Schaefer, J. Macromolecules 1992, 25, 4084-4091.
Afeworki, M.; Schaefer, J. Macromolecules 1992, 25, 4092-4096.
Afeworki, M.; Schaefer, J. Macromolecules 1992, 25, 4097-4099.
Afeworki, M.; Vega, S.; Schaefer, J. Macromolecules 1992, 25, 4100-4106.
Ardenkjaer-Larsen, J. H.; Fridlund, B.; Gram, A.; Hansson, G.; Hansson, L.; Lerche, M. H.; Servin, R.; Thaning, M.; Golman, K. Proc. Natl. Acad. Sci. U.S.A. 2003, 100, 10158-10163.
Bagryanskaya et al., Russian Chemical Reviews, 69:925-45 (2000).
Bajaj, V. S.; Farrar, C. T.; Mastovsky, I.; Vieregg, J.; Bryant, J.; Elena, B.; Kreischer, K. E.; Temkin, R. J.; Griffin R. G. J. Magn. Reson. 2003, 160, 85 90.
Bajaj, V. S.; Mak, M.; Hornstein, M. K.; Belenky, M.; Herzfeld, J.; Temkin, R. J.; Griffin, R. G. Biophys. J. 2005, 88, 203A-203A. (abstract only).
Becerra, L. R.; Gerfen, G. J.; Temkin, R. J.; Singel, D. J.; Griffin, R. G. Phys. Rev. Lett. 1993, 71, 3561-3564.
Farrar et al., "Mechanism of Dynamic Nuclear Polarization in High magnetic Fields," Journal of Chemical Physics 2001, 114(11):4922-4933.
Farrar, C.T.; Hall, D.A.; Gerfen, G. J.; Rosay, M.; Ardenkjaer-Larsen, J. H.; Griffin, R. G. J. Magn. Reson. 2000, 144, 134-141.
Ferguson, D. B.; Krawietz, T. R.; Haw, J. F. J. Magn. Reson. Ser. A 1994, 109, 273-275.
Ferguson, D.B.; Haw, J. F. Anal. Chem. 1995, 67, 3342-3348.
Franks, W. T.; Zhou, D. H.; Wylie, B. J.; Money, B. G.; Graesser, D. T.; Frericks, H. L.; Sahota, G.; Rienstra, C. M. J. Am. Chem. Soc. 2005, 127, 12291-12305.
Gagnaire et al., "Regulation by Potassium Ions of Spin Exchange and Dipolar Splitting in Biradical. A Simple Allosteric System," Tetrohedron Letters 1989, 3047):6507-6510.
Gerfen, G. J.; Becerra, L. R.; Hall, D. A.; Griffin, R. G.: Temkin, R. J.; Singel, D. J. J. Chem. Phys. 1995, 102, 9494-9497.
Hall, D. A.; Maus, D. C.; Gerfen, G. J.; Inati, S. J.; Becerra, L. R.; Dahlquist, F. W.; Griffin, R. G. Science 1997, 276,930-932.
Henstra, "High Dynamic Nuclear Polarization at Room Temperature," Chemical Physics Letters 1990, 165(1):6-10.
Hu, K.-N.; Song, C.; Swager, T. M.; Griffin, R. G. J. Chem. Phys. 2008, 128, 052302.
Hu, K.-N.; Yu, H.-h.; Swager, T. M.; Griffin, R. G. J. Am. Chem. Soc. 2004, 126, 10844-10845.
Igumenova, T. I.; McDermott, A. E.; Zilm, K. W.; Martin, R. W.; Paulson, E. K.; Wand, A. J. J. Am. Chem. Soc. 2004, 126, 6720-6727.
Kirste et al., J. Am. Chem. Soc. 1982, 104:3850-58.
Mak, M. L.; Bajaj, V. S.; Hornstein, M. K.; Belenky, M.; Temkin, R. J.; Griffin, R. G.; Herzfeld, J. Biophys. J. 2005, 88, 506A-506A. (abstract only).
Martin, R. W.; Zilm, K. W. J. Magn. Reson. 2003, 165, 162-174.
Nelson, R.; Sawaya, M. R.; Balbirnie, M.; Madsen, A. O.; Riekel, C.; Grothe, R.; Eisenberg, D. Nature 2005, 435, 773-778.
Reddy, T. J.; Iwama, T.; Halpern, H. J.; Rawal, V. H. J. Org. Chem. 2002, 67, 4635-4639.
Rosay et al., "High Frequency Dynamic Nuclear Polarization in MAS Spectra of membrane and Soluble Proteins," J. Americ. Chem. Soc. 2003, 125:13626-27.
Rosay, M.; Zeri, A. C.; Astrof, N. S.; Opella, S. J.; Herzfeld, J.; Griffin, R. G., J. Am. Chem. Soc. 2001, 123, 1010-1011.
Rosay et al., "Two-Dimensional $^{13}C$-$^{13}C$ Spectroscopy with Magic Angle Spinning and Dynamic Nuclear Polarization," J. Am. Chem. Soc. 2002, 124, 3214-3215.
Singel, D. J.; Seidel, H.; Kendrick, R. D.; Yannoni, C. S. J. Magn. Reson. 1989, 81, 145-161.
Song et al., "TOTAPOL: A Bioradical Polarizing Agent for Dynamic Nuclear Polarization Experiments in Aqueous Media," JACS Aug. 16, 2006, vol. 128, No. 35, pp. 11385-11390.
Turro et al., "An Electron Spin Polarization Study of the Interaction of Photoexcited Triplet Molecules with Mono- and Polynitroxyl Stable Free Radicals," J. Phys. Chem. 1993, 97:1138-1146.
Van Den Heuvel, "Transient Oscillations in Pulsed Dynamic Nuclear Polarization," Chemnical Physics Letters 1992, 188(3-4):194-200.
Van Der Wel, P.; Hu, K.-N.; Lewandowski, J.; Griffin, R. G., Dynamic Polarization of Amyloidogenic Peptide Nancrystals: GNNQQNY A Core Segement of the Yeast Prion Protein, Sup 35p., J. of American Chemical Soc. 2006, vol. 128, pp. 10840-10846.

* cited by examiner

2,2,6,6-tetramethylpiperidine-N-oxyl radical (TEMPO)

Synthesis from amine:

Examples of commercially available derivatives:

R = OH, NH₂, NHAc
CN, NCS, COOH

X = Cl, Br, I

2,2,5,5-tetramethylpyrrolidine-N-oxyl radical

Examples of commercially available derivatives:

Related synthesis of proxyl nitroxides:

4,4-dimethyloxazolidine-N-oxyl (a doxyl nitroxide)

Synthesis:

Nitronyl Nitroxides

Synthesis:

Synthesis:

Diaryl Nitroxides

Synthesis:

Scheme 1

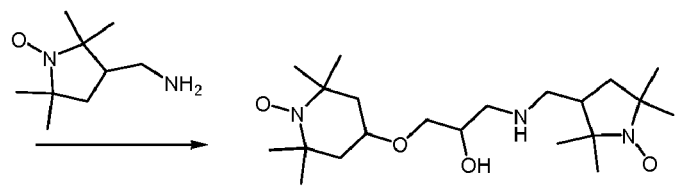

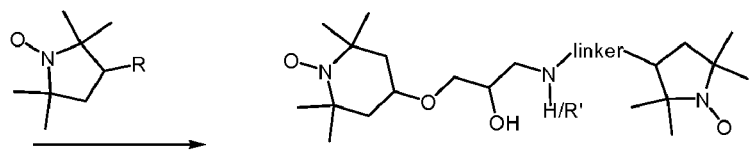

Where R contains a linker with a primary or secondary amine,
so R = linker - NH₂ or linker - NHR'.

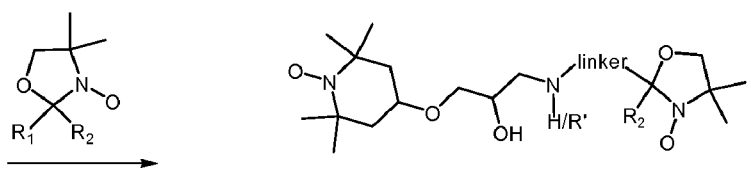

Where R₁ contains a linker with a primary or secondary amine,
so R₁ = linker - NH₂ or linker - NHR'.

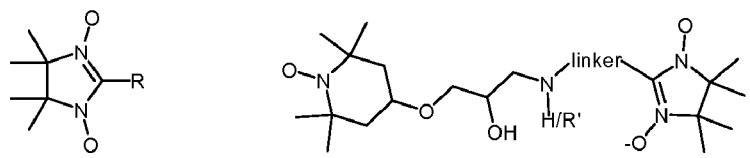

Where R contains a linker with a primary or secondary amine,
so R = linker - NH₂ or linker - NHR'.

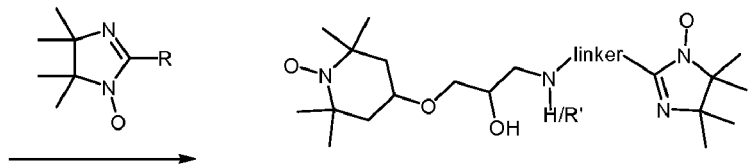

Where R contains a linker with a primary or secondary amine,
so R = linker - NH₂ or linker - NHR'.

Variations on Scheme 1

FIGURE 7 (continued)

BIRADICAL POLARIZING AGENTS FOR DYNAMIC NUCLEAR POLARIZATION

PRIORITY CLAIM

The present application is a national phase application under 35 U.S.C. §371 of PCT International Application No. PCT/US2007/068659, filed May 10, 2007, which claims priority under 35 U.S.C. §119(e) to U.S. provisional patent application, U.S. Ser. No. 60/747,102, filed May 12, 2006. The entire contents of each of these priority applications is incorporated herein by reference.

GOVERNMENT FUNDING

The inventions described herein were made with support from funding from the National Institutes of Health, Grant No. EB-002804 and the Office of Naval Research, Grant No. N00014-03-1-0897. The U.S. Government therefore has certain rights in these invention.

BACKGROUND OF THE INVENTION

The last decade has witnessed a renaissance in the development of approaches to prepare samples with high nuclear spin polarizations with the goal of increasing signal intensities in nuclear magnetic resonance (NMR) spectra and magnetic resonance imaging (MRI) images. These approaches have included high frequency, microwave driven dynamic nuclear polarization (DNP)[1-9], para hydrogen induced polarization (PHIP)[10,11], polarization of noble gases such as He, Xe[12-14] and more recently Kr[15], and optically pumped nuclear polarization of semiconductors[16-18] and photosynthetic reaction centers and other proteins[19-22]. Dynamic nuclear polarization is an approach in which the large spin polarization in an electron spin system is transferred to a nuclear spin reservoir via microwave irradiation of the electron paramagnetic resonance (EPR) spectrum. The electron spin system in DNP is provided by a endogenous or exogenous paramagnetic polarizing agent. To date, most polarizing agents that have been used for DNP have been monoradicals (e.g., TEMPO based radicals, trityl radicals, etc.). In U.S. Patent Publication No. 20050107696 we recently described the use of a biradical (bis-TEMPO-2-ethyleneglycol (BT2E), where TEMPO is 2,2,6,6-tetramethylpiperidin-1-oxyl and n=2 indicates a tether of two ethylene glycol units) which produced DNP enhancements of ~175 at 90 K and 5 T[23]. This was accomplished at a reduced radical concentration (~5 mM biradicals or 10 mM electron spins, as opposed to ~40 mM when using monomeric TEMPO), thus reducing the electron nuclear dipolar broadening. While the BT2E biradical provided a number of benefits over known monoradical polarizing agents, there remains a need in the art for improved polarizing agents and in particular improved biradical polarizing agents. Superscript numbers refer to the attached reference list. The contents of all of these references are incorporated herein by reference.

SUMMARY OF THE INVENTION

In one aspect, the present invention provides methods for performing dynamic nuclear polarization using biradicals having the structure of formula (I):

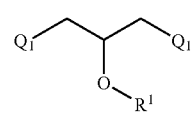

wherein
$Q_1$ is the group $—X_1-L_1-M_1$;
$Q_2$ is the group $—X_2-L_2-M_2$, where $Q_1$ and $Q_2$ may be the same or different;
$R^1$ is hydrogen; a suitable hydroxyl protecting group; substituted or unsubstituted, cyclic or acyclic $C_{1-6}$ aliphatic; substituted or unsubstituted, cyclic or acyclic $C_{1-6}$ heteroaliphatic; substituted or unsubstituted aryl, substituted or unsubstituted heteroaryl; acyl; $C_{1-6}$ alkyl sulfonyl; $C_{1-6}$ alkyl sulfinyl; substituted or unsubstituted aryl sulfinyl; or substituted or unsubstituted aryl sulfonyl;
$X_1$ and $X_2$ are independently selected from $—O—$, $—S—$, or $—N(R^2)—$, wherein $R^2$ is hydrogen, a suitable amino protecting group; substituted or unsubstituted amino; substituted or unsubstituted hydroxyl; substituted or unsubstituted, cyclic or acyclic $C_{1-6}$ aliphatic; substituted or unsubstituted, cyclic or acyclic $C_{1-6}$ heteroaliphatic; substituted or unsubstituted aryl; substituted or unsubstituted heteroaryl; acyl; $C_{1-6}$ alkyl sulfonyl; $C_{1-6}$ alkyl sulfinyl; substituted or unsubstituted aryl sulfinyl; or substituted or unsubstituted aryl sulfonyl;
$L_1$ and $L_2$ are independently selected from a direct bond; substituted or unsubstituted, cyclic or acyclic $C_{1-6}$ aliphatic; or substituted or unsubstituted, cyclic or acyclic $C_{1-6}$ heteroaliphatic; and
$M_1$ and $M_2$ are, independently, a substituted or unsubstituted, cyclic or acyclic nitroxide.

In general, the methods involve (a) providing a frozen sample in a magnetic field, wherein the frozen sample includes a biradical of formula (I) and an analyte with at least one spin half nucleus; (b) polarizing the at least one spin half nucleus of the analyte by irradiating the frozen sample with radiation having a frequency that excites electron spin transitions in the biradical; (c) optionally melting the sample to produce a molten sample; and (d) detecting nuclear spin transitions in the at least one spin half nucleus of the analyte in the frozen or molten sample. In certain embodiments, the analyte is a molecule (e.g., a protein) that is being studied by solid- or liquid-state NMR. In other embodiments, the analyte is an imaging agent that is being used for MRI in which case the step of detecting is performed after the polarized imaging agent has been administered to the subject being imaged.

In another aspect, the present invention provides biradicals having the structure of formula (I) with the proviso that $Q_1$ and $Q_2$ are different when $X_1$ and $X_2$ are $—O—$.

In yet another aspect, the present invention provides a method of making biradicals having the structure of formula (IA):

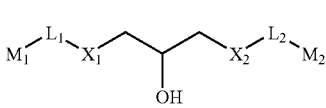

wherein
$X_1$ and $X_2$ are independently selected from $—O—$, $—S—$, or $—N(R^2)—$, wherein $R^2$ is hydrogen, a suitable amino protecting group; substituted or unsubstituted amino; substituted or unsubstituted hydroxyl; substituted or unsubstituted, cyclic or acyclic $C_{1-6}$ aliphatic; substituted or unsubstituted; cyclic or acyclic $C_{1-6}$ heteroaliphatic; substituted or unsubstituted aryl, substituted or unsubstituted heteroaryl, acyl; $C_{1-6}$ alkyl sulfonyl; $C_{1-6}$ alkyl sulfinyl; substituted or unsubstituted aryl sulfinyl; or substituted or unsubstituted aryl sulfonyl;

$L_1$ and $L_2$ are independently selected from a direct bond; substituted or unsubstituted, cyclic or acyclic $C_{1-6}$ aliphatic; or substituted or unsubstituted, cyclic or acyclic $C_{1-6}$ heteroaliphatic; and $M_1$ and $M_2$ are, independently, a substituted or unsubstituted, cyclic or acyclic nitroxide. According to this aspect, the method comprises steps of (i) reacting a compound of formula:

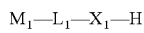

with a compound of formula:

wherein $LG_1$ is a suitable leaving group, to provide a compound of formula:

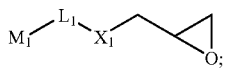

and then (ii) reacting the compound of formula:

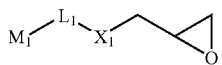

with a compound of formula:

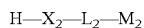

to provide a biradical of formula (IA).

Definitions

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987; the entire contents of each of which are incorporated herein by reference.

It will be appreciated that the inventive compound as described herein may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds.

The term "acyl," as used herein, refers to a group having the general formula $—C(=O)R^o$, where $R^o$ is substituted or unsubstituted hydroxyl, substituted or unsubstituted thiol, substituted or unsubstituted amino, substituted or unsubstituted, cyclic or acyclic aliphatic, substituted or unsubstituted, cyclic or acyclic heteroaliphatic, substituted or unsubstituted aryl, or substituted or unsubstituted heteroaryl. Exemplary acyl groups include carboxylic acids ($—CO_2H$), ketones (such as an acetyl group $[—C(=O)CH_3]$, esters, amides, carbonates, carbamates, and ureas. Acyl substituents include, but are not limited to, any of the substituents described herein, that result in the formation of a stable moiety (for example, an aliphatic group substituted with one or more aliphatic, alkyl, alkenyl, alkynyl, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "aliphatic," as used herein, includes both saturated and unsaturated, nonaromatic, straight chain (i.e., unbranched), branched, acyclic, cyclic (i.e., carbocyclic), or polycyclic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-6 carbon atoms, or 2-6 carbon atoms. In certain embodiments, an aliphatic group has 1-5 or 2-5 carbon atoms. In certain embodiments, an aliphatic group has 1-4 or 2-4 carbon atoms. In certain embodiments, an aliphatic group has 1-3 or 2-3 carbon atoms. In certain embodiments, an aliphatic group has 1-2 carbon atoms. In certain embodiments, an aliphatic group has 1 carbon atom. In certain embodiments, an aliphatic group has 2 carbon atoms. Aliphatic group substituents include, but are not limited to, any of the substituents described herein, that result in the formation of a stable moiety (for example, an aliphatic group substituted with one or more aliphatic, alkyl, alkenyl, alkynyl, heteroaliphatic, heterocyclic, aryl, heteroaryl, acyl, sulfinyl, sulfonyl, oxo, imino, thiooxo, phosphino, cyano, amino, azido, nitro, hydroxy, thio, and/or halo groups).

The term "alkyl," as used herein, refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-6 carbon atoms. In another embodiment, the alkyl group employed contains 1-5 carbon atoms. In still other embodiments, the alkyl group contains 1-4 carbon atoms. In yet another embodiments, the alkyl group contains 1-3 carbons. In yet other embodiments, the alkyl group contains 1-2 carbons. In yet other embodiments, the alkyl group contains 1 carbon atom. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, and the like, which may bear one or more sustitutents. Alkyl group substituents include, but are not limited to, any of the substituents described herein, that result in the formation of a stable moiety (for example, an alkyl group substituted with one or more aliphatic, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "alkenyl," as used herein, denotes a monovalent group derived from a straight- or branched-chain hydrocarbon moiety having at least one carbon-carbon double bond by the removal of a single hydrogen atom. In certain embodiments, the alkenyl group employed in the invention contains 2-6 carbon atoms. In some embodiments, the alkenyl group employed in the invention contains 2-5 carbon atoms. In another embodiment, the alkenyl group employed contains 2-4 carbon atoms. In still other embodiments, the alkenyl group contains 2-3 carbon atoms. In yet another embodiments, the alkenyl group contains 2 carbons. Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety (for example, an alkenyl group substituted with one or more aliphatic, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "alkynyl," as used herein, refers to a monovalent group derived from a straight- or branched-chain hydrocarbon having at least one carbon-carbon triple bond by the removal of a single hydrogen atom. In certain embodiments, the alkynyl group employed in the invention contains 2-6 carbon atoms. In some embodiments, the alkynyl group employed in the invention contains 2-5 carbon atoms. In another embodiment, the alkynyl group employed contains 2-4 carbon atoms. In still other embodiments, the alkynyl group contains 2-3 carbon atoms. In still other embodiments, the alkynyl group contains 2 carbon atoms. Representative alkynyl groups include, but are not limited to, ethynyl, 2-propynyl (propargyl), 1-propynyl, and the like, which may bear one or more substituents. Alkynyl group substituents include, but are not limited to, any of the substituents described herein, that result in the formation of a stable moiety (for example, an alkynyl group substituted with one or more aliphatic, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "amino," as used herein, refers to a group of the formula (—$NH_2$). A "substituted amino" refers to a group of the formulae (—$NHR^h$) or (—$NR^h_2$), wherein $R^h$ can be any substitutent except hydrogen which result in the formation of a stable moiety (for example, an amino group substituted with one or more aliphatic, alkyl, alkenyl, alkynyl, heteroaliphatic, heterocyclic, aryl, heteroaryl, acyl, sulfinyl, sulfonyl, amino, nitro, hydroxy, and/or thio groups). A "suitable amino-protecting group," as used herein, is well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'- dithiobenzyloxycarbonylamino)acetamide, 3-(p-hydroxyphenyl)propanamide, 3-(o-nitrophenyl) propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

The term "aryl," as used herein, refer to stable aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic $C_4$—$C_{20}$ aromatic ring system having one, two, or three aromatic rings which include, but not limited to, phenyl, biphenyl, naphthyl, and the like, which may bear one or more substituents. Aryl substituents include, but are not limited to, any of the substituents described herein, that result in the formation of a stable moiety (for example, an aryl group substituted with one or more aliphatic, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "azido," as used herein, refers to a group of the formula (—$N_3$).

The term "cyano," as used herein, refers to a group of the formula (—CN).

The term "direct bond" or "bond" refers to a single, double or triple bond between two groups. In certain embodiments, a "direct bond" refers to a single bond between two groups.

The terms "halo" and "halogen" as used herein refer to an atom selected from fluorine (fluoro, —F), chlorine (chloro, —Cl), bromine (bromo, —Br), and iodine (iodo, —I).

The term "heteroaliphatic," as used herein, includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. As will be appreciated by one of ordinary skill in the art, "heteroaliphatic" is intended herein to include, but is not limited to, heteroalkyl, heteroalkenyl, heteroalkynyl, and heterocyclyl moieties. Thus, as used herein, the term "heteroalkyl" includes straight, branched and cyclic alkyl groups, as defined herein, which are optionally substituted with one or more functional groups, and that contain one or more oxygen, sulfur, nitrogen, phosphorus, or silicon atoms, e.g., in place of carbon atoms. An analogous convention applies to other generic terms such as "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-6 carbon atoms, or 2-6 carbon atoms. In certain embodiments, a heteroaliphatic group has 1-5 or 2-5 carbon atoms. In certain embodiments, a heteroaliphatic group has 1-4 or 2-4 carbon atoms. In certain embodiments, a heteroaliphatic group has 1-3 or 2-3 carbon atoms. In certain embodiments, a heteroaliphatic group has 1-2 carbon atoms. In certain embodiments, an heteroaliphatic group has 1 carbon atom. In certain embodiments, a heteroaliphatic group has 2 carbon atoms. Heteroaliphatic group substituents include, but are not limited to, any of the substituents described herein, that result in the formation of a stable moiety (for example, a heteroaliphatic group substituted with one or more aliphatic, alkyl, alkenyl, alkynyl, heteroaliphatic, heterocyclic, aryl, heteroaryl, acyl, sulfinyl, sulfonyl, oxo, imino, thiooxo, phosphino, cyano, amino, azido, nitro, hydroxy, thio, and/or halo groups).

The term "heteroaryl," as used herein, refer to stable aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety (for example, a heteroaryl group substituted with one or more aliphatic, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "heterocyclic," or "heterocyclyl," as used herein, refers to an non-aromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety (for example, a heterocyclic group substituted with one or more aliphatic, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "hydroxy," or "hydroxyl," as used herein, refers to a group of the formula (—OH). A "substituted hydroxyl" refers to a group of the formula (—OR$^i$), wherein R$^i$ can be any substitutent except hydrogen which results in a stable moiety (for example, a hydroxy group substituted with a suitable hydroxyl protecting group, an aliphatic, alkyl, alkenyl, alkynyl, heteroaliphatic, heterocyclic, aryl, heteroaryl, acyl, sulfinyl, and/or sulfonyl group). A "suitable hydroxyl protecting group" as used herein, is well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkylp-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

The term "imino," as used herein, refers to a group of the formula (=NR$^r$), wherein R$^r$ corresponds to hydrogen or any substitutent as described herein, that results in the formation of a stable moiety (for example, a suitable amino protecting group; substituted or unsubstituted amino; acyl; cyclic or acylic, branched or unbranched, substituted or unsubstituted alkyl; cyclic or acylic, branched or unbranched, substituted or unsubstituted alkenyl; cyclic or acylic, branched or unbranched, substituted or unsubstituted alkynyl; cyclic or acylic, branched or unbranched, substituted or unsubstituted heteroalkyl; cyclic or acylic, branched or unbranched, substituted or unsubstituted heteroalkenyl; cyclic or acylic, branched or unbranched, substituted or unsubstituted heteroalkynyl; substituted or unsubstituted aryl; or substituted or unsubstituted heteroaryl).

The term "isocyano," as used herein, refers to a group of the formula (—NC).

The term "nitro," as used herein, refers to a group of the formula (—NO$_2$).

The term "nitroxide," as used herein, refers to a stable nitroxide group which may be cyclic or acyclic. In certain embodiments, a stable nitroxide refers to a chemically stable nitroxide which may be obtained in pure form, stored, and handled in the laboratory. In certain embodiments, a stable nitroxide refers to a cyclic or acyclic nitroxide which contains two groups which do not contain alpha hydrogens. Exemplary cyclic or acyclic nitroxides are provided in Keana, *Chemical Reviews* (1978) 78:37-64, the entirety of which is incorporated herein by reference, which optionally may be synthetically modified in order to provide a suitable linker group (such as —L$_1$—X$_1$— or —L$_2$—X$_2$— as described herein).

The term "oxo," as used herein, refers to a group of the formula (=O).

The term "stable moiety," as used herein, preferably refers to a moiety which possess stability sufficient to allow manufacture, and which maintains its integrity for a sufficient period of time to be useful for the purposes detailed herein.

The term "thio," or "thiol," as used herein, refers to a group of the formula (—SH). A "substituted thiol" refers to a group of the formula (—SR$^r$), wherein R$^r$ is any substitutent, except hydrogen, which results in the formation of a stable moiety (for example, a thio group substituted with one or more aliphatic, alkyl, alkenyl, alkynyl, heteroaliphatic, heterocyclic, aryl, heteroaryl, acyl, sulfinyl, and/or sulfonyl).

The term "thiooxo," as used herein, refers to a group of the formula (=S).

The term "suitable leaving group," as used herein, refers to the halogens —Br, —Cl, and —I, and "activated" hydroxyl groups of the formula —OR$^v$, wherein R$^v$ is acyl, alkyl sulfonyl, or aryl sulfonyl. Exemplary activated (alkyl or aryl sulfonyl) hydroxyl groups include O-trifluoromethylsulfonyl (—OTf), O-tolylsulfonyl (—OTs), O-methanesulfonyl (—OMs), O-(4-nitrophenylsulfonyl) (—ONos), and O-(2-nitrophenylsulfonyl) (—ONs), and the like. In certain embodiments, a suitable leaving group is —Br, —Cl, —I, —OR$^w$, —OC(O)R$^w$, —OS(O)$_2$R$^w$, wherein each R$^w$ is substituted or unsubstituted, cyclic or acyclic C$_{1-6}$ aliphatic; substituted or unsubstituted, cyclic or acyclic C$_{1-6}$ heteroaliphatic; substituted, unsubstituted aryl; or substituted or unsubstituted heteroaryl.

The term "sulfinyl," as used herein, refers to a group of the formula R$^f$—S(=O)— wherein R$^f$ may be an optionally substituted aliphatic, heteroaliphatic, aryl, or heteroaryl. The term "alkyl sulfinyl" refers to a sulfinyl group where R$^f$ may be an optionally substituted alkyl group. The term "aryl sulfinyl" refers to a sulfinyl group where R$^f$ may be an optionally substituted aryl or heteroaryl group.

The term "sulfonyl," as used herein, refers the group of the formula R$^g$—S(=O)$_2$—, wherein Rg may be an optionally substituted aliphatic, heteroaliphatic, aryl, or heteroaryl. The term "alkyl sulfonyl" refers to a sulfonyl group where R$^g$ may be an optionally substituted alkyl group. The term "aryl sulfonyl" refers to a sulfonyl group where R$^g$ may be an optionally substituted aryl or heteroaryl. Exemplary aryl or alkyl sulfonyl groups include tosyl (toluene sulfonyl, CH$_3$C$_6$H$_4$SO$_2$—), mesyl (methyl sulfonyl, CH$_3$SO$_2$—), and trifluoromethanesulfonyl (CF$_3$SO$_2$—).

BRIEF DESCRIPTION OF THE DRAWING

FIG. 3 (bottom) shows the field dependence of the $^1$H enhancement in a DNP experiment using the biradical polarizing agent TOTAPOL (solid circles). The field dependence from BT2E is essentially identical to TOTAPOL (open circles).

FIG. 7 also shows some exemplary variations on the synthesis of Scheme 1 that employ different nitroxide radicals.

DESCRIPTION OF CERTAIN PREFERRED EMBODIMENTS

Figure 1:
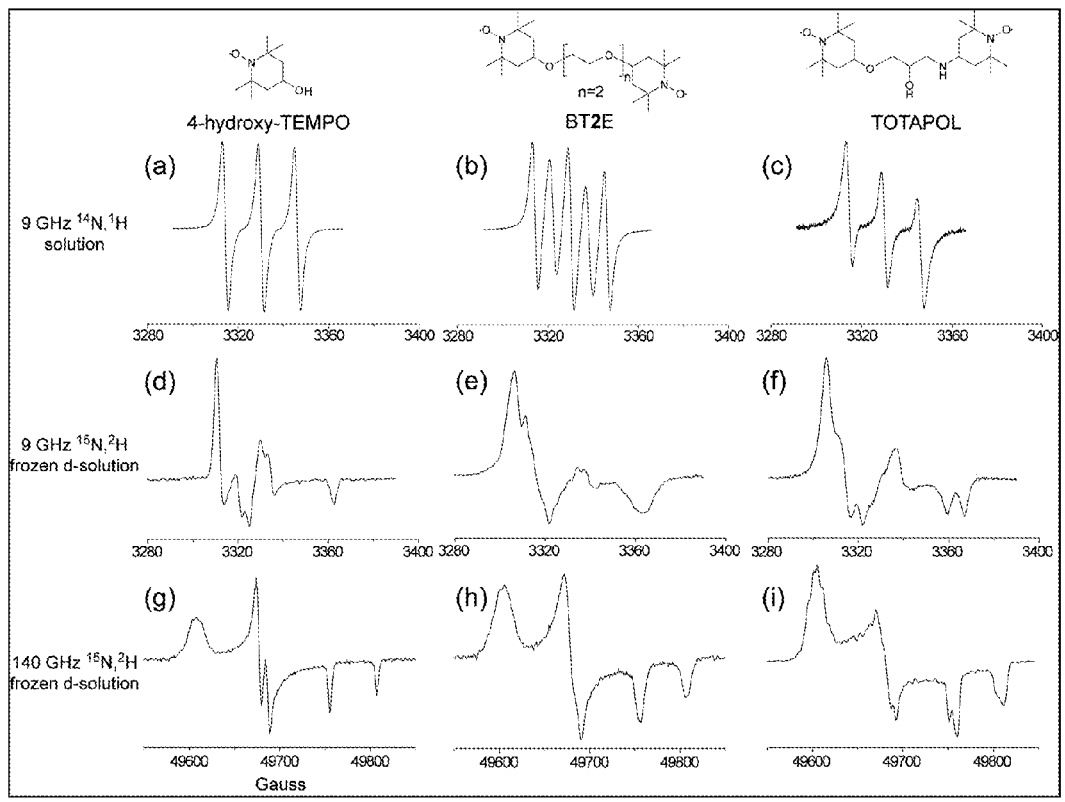
FIG. 1 shows the 9 and 140 GHz EPR spectra of TEMPO, BT2E and TOTAPOL with the molecular structures shown in the top line. (a)-(c) are 9 GHz solution spectra illustrating the extra two lines in the spectrum from the transient proximity of two TEMPO moieties with a strong electron-electron J-coupling [compare (a) with (b)]. These lines in TOTAPOL are severely broadened in (c) by shorter life time of the transient proximity due to rigidity of the tether, which cannot bend the biradical easily. (d)-(f) illustrate the 9 GHz spectra obtained from frozen solutions at 77 K, and (g)-(i) illustrate the 140 GHz spectra from the same solutions frozen at 20 K.

The sensitivity in solid-state NMR (ssNMR) experiments can be enhanced by two to three orders of magnitude by dynamically polarizing the nuclear spin system prior to recording the NMR spectrum. This enhancement can be transferred into the liquid-state (e.g., liquid-state NMR or MRI) by melting the solid sample after polarization (e.g., as described herein and in a PCT patent application that we filed on May 10, 2007 entitled "Temperature-Jump Dynamic Nuclear Polarization", the contents of which are incorporated herein by reference). For MRI applications, at least a portion of the molten sample that includes a polarized analyte is administered into the subject being imaged prior to imaging.

The DNP procedure involves microwave irradiation of the electron paramagnetic resonance (EPR) spectrum of either an endogenous or exogenous paramagnetic species present in a sample, and results in the transfer of the greater spin polarization of the electrons to the nuclei of surrounding molecules. While the methods described herein are not limited to any specific magnetic field and the DNP procedure could be performed at low magnetic fields, the performance of dynamic nuclear polarization (DNP) experiments at the high magnetic fields used in contemporary NMR experiments (e.g., 5-20 T) is affected by the following three factors.

First, a high frequency (140-600 GHz), high power (~10 watts) microwave source is typically used to drive the continuous-wave (CW) DNP transitions associated with the second order electron-nuclear dipolar interactions. To date this has been achieved by utilizing gyrotrons[24-27] since they operate in the requisite frequency range and produce suitable microwave powers.

Second, the relaxation times of the spin systems in the experiment dictate that it be optimally performed at low temperatures (usually ≦90 K). When obtaining high resolution ssNMR spectra of solids, magic-angle spinning (MAS) is preferably incorporated into the experiment[28-32]. Thus, multiple resonance—i.e., $^1H$, $^{13}C$, $^{15}N$ and $e^-$—low temperature MAS probes may be required for optimal execution of certain DNP experiments.

The third factor is the nature of the paramagnetic polarizing agent. Preferably, the polarizing agent should: (a) be compatible with the polarization mechanism that yields the optimal signal enhancement, namely the three-spin thermal mixing (TM)[28,33] or cross effect (CE)[34-40], (b) be useful in polarizing a large array of analytes ranging from small molecules to proteins, (c) produce large signal enhancements at a reduced concentration of paramagnetic species, and (d) be soluble in aqueous media. As noted above, we have previously described the use of a biradical that satisfies the first three of these criteria and yields improved DNP enhancements[23]. In particular, we reported that bis-TEMPO-2-ethyleneglycol (BT2E), where TEMPO is 2,2,6,6-tetramethylpiperidin-1-oxyl and n=2 indicates a tether of two ethylene glycol units, produced DNP enhancements of 175 at 90 K and 5 T.

The present invention provides polarizing agents that satisfy the first three criteria as well as the fourth requirement (i.e., solubility in aqueous media). This last criterion is significant since it opens up a vast number of DNP-NMR and DNP-MRI applications that rely on aqueous media.

In one aspect, the present invention provides methods for performing dynamic nuclear polarization using biradicals having the formula (I):

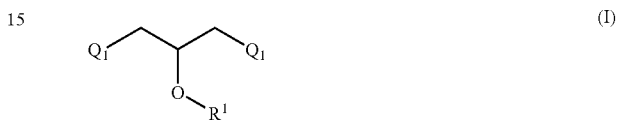

wherein
Q$_1$ is the group —X$_1$—L$_1$—M$_1$;
Q$_2$ is the group —X$_2$—L$_2$—M$_2$, where Q$_1$ and Q$_2$ may be the same or different;
R$^1$ is hydrogen; a suitable hydroxyl protecting group; substituted or unsubstituted, cyclic or acyclic C$_{1-6}$ aliphatic; substituted or unsubstituted, cyclic or acyclic C$_{1-6}$ heteroaliphatic; substituted or unsubstituted aryl, substituted or unsubstituted heteroaryl; acyl; C$_{1-6}$ alkyl sulfonyl; C$_{1-6}$ alkyl sulfinyl; substituted or unsubstituted aryl sulfinyl; or substituted or unsubstituted aryl sulfonyl;
X$_1$ and X$_2$ are independently selected from —O—, —S—, or —N(R$^2$)—, wherein R$^2$ is hydrogen, a suitable amino protecting group; substituted or unsubstituted amino; substituted or unsubstituted hydroxyl; substituted or unsubstituted, cyclic or acyclic C$_{1-6}$ aliphatic; substituted or unsubstituted, cyclic or acyclic C$_{1-6}$ heteroaliphatic; substituted or unsubstituted aryl; substituted or unsubstituted heteroaryl; acyl; C$_{1-6}$ alkyl sulfonyl; C$_{1-6}$ alkyl sulfinyl; substituted or unsubstituted aryl sulfinyl; or substituted or unsubstituted aryl sulfonyl;
L$_1$ and L$_2$ are independently selected from a direct bond; substituted or unsubstituted, cyclic or acyclic C$_{1-6}$ aliphatic; or substituted or unsubstituted, cyclic or acyclic C$_{1-6}$ heteroaliphatic; and
M$_1$ and M$_2$ are, independently, a substituted or unsubstituted, cyclic or acyclic nitroxide.

In general, the methods involve (a) providing a frozen sample in a magnetic field, wherein the frozen sample includes a biradical of formula (I) and an analyte with at least one spin half nucleus; (b) polarizing the at least one spin half nucleus of the analyte by irradiating the frozen sample with radiation having a frequency that excites electron spin transitions in the biradical; (c) optionally melting the sample to produce a molten sample; and (d) detecting nuclear spin transitions in the at least one spin half nucleus of the analyte in the frozen or molten sample. In certain embodiments, the methods further comprise a step of freezing a sample in a magnetic field to provide the frozen sample in a magnetic field. In one such embodiment, the sample is melted prior to detection and the freezing, polarizing, melting and detecting steps are repeated at least once.

In certain embodiments, the analyte is a molecule (e.g., a protein) that is being studied by solid- or liquid-state NMR. In other embodiments, the analyte is an imaging agent that is being used for MRI. In such embodiments, the step of detecting is performed after at least a portion of the molten sample which comprises the polarized imaging agent has been administered to the subject being imaged. In general, the frozen sample may include any solvent; however, in certain embodiments, the frozen sample includes an amount of water, e.g., at least 50%, 60%, 70%, 80%, 90%, 95%, 99% or 100% by volume of water.

In one embodiment, the methods of the present invention do not include a step of melting the sample to produce a molten sample. According to such embodiments, the sample is frozen in the detection step and the nuclear spin transitions in the at least one spin half nucleus of the analyte in the frozen sample are detected by solid-state NMR.

In another embodiment, the methods of the present invention do include a step of melting the sample to produce a molten sample. According to such embodiments, the sample is molten in the detection step and the nuclear spin transitions in the at least one spin half nucleus of the analyte in the molten sample may be detected by liquid-state NMR. Alternatively, the nuclear spin transitions in the at least one spin half nucleus of the analyte in the molten sample may be detected by MRI. According to this last embodiment, at least a portion of the molten sample that includes polarized analyte is administered (e.g., by injection, ingestion, inhalation, etc.) to a subject prior to detection. In certain embodiments (e.g., when the biradical is toxic) the polarized analyte may be separated from the biradical prior to administration. U.S. Pat. No. 6,311,086 (the contents of which are incorporated herein by reference) describes several methods for achieving such a separation (e.g., physical and chemical separation or extraction techniques).

In general, the methods may be used to polarize any analyte. Without limitation, the analyte may be a protein or nucleic acid. Numerous solid-state and liquid-state NMR methods have been developed to study the structures of these biomolecules, e.g., one dimensional techniques, multi-dimensional techniques, including without limitation techniques that rely on NOESY, ROESY, TOCSY, HSQC, HMQC, etc. type polarization transfers and combinations thereof. Any of these techniques and variants thereof may benefit from the enhanced NMR signals that can be provided by the inventive methods. The inventive methods may also be advantageously used to improve the detection of analytes (e.g., metabolites) that are present in a sample at low concentrations (e.g., less than 1 μM, less than 100 nM, less than 10 nM or even less than 1 nM). When the analyte is being used as an imaging agent for an MRI experiment then it will preferably include at least one spin half nucleus with a long $T_1$ relaxation time. This will ensure that the enhancement is not lost by relaxation in between the polarizing and detecting steps. For example, U.S. Pat. No. 6,311,086 describes imaging agents that include spin half nuclei with $T_1$ relaxation times of at least 6 seconds at 310 K in $D_2O$ in a magnetic field of 7 T. It will be appreciated that any of the imaging agents that are described in U.S. Pat. No. 6,311,086 may be used as an analyte in an inventive method. It is also to be understood that any known MRI technique may be used to image the spatial distribution of a polarized analyte once administered to a subject (e.g., see MRI in Practice Ed. by Westerbrook et al., Blackwell Publishing, Oxford, UK, 2005, the contents of which are incorporated herein by reference).

Any spin half nucleus within the analyte may be polarized according to the inventive methods. In one embodiment, the spin half nucleus is a $^1H$ nucleus. In one embodiment, the spin half nucleus is a $^{13}C$ nucleus. In one embodiment, the spin half nucleus is a $^{15}N$ nucleus. In one embodiment, the spin half nucleus is a $^{19}F$ nucleus. The spin half nucleus may be present in the analyte at natural abundance levels. Alternatively, stronger signals may be obtained if the spin half nucleus (e.g., $^{13}C$, $^{15}N$, $^{19}F$, etc.) is enriched at one or more positions within the analyte. A variety of methods are known in the art for enriching one or more sites of an analyte (e.g., a protein, nucleic acid, metabolite, imaging agent, etc.). When the at least one spin half nucleus has a y-value smaller than that of $^1H$ (e.g., $^{13}C$, $^{15}N$, $^{19}F$, etc.) then in certain embodiments, the step of polarizing may further involve irradiating the frozen sample with radiation having a frequency that causes cross-polarization between a $^1H$ nucleus present in the sample (e.g., without limitation from $^1H_2O$) and the at least one spin half nucleus of the analyte.

The inventive methods may be performed under any magnetic field strength. In one embodiment the field may have a strength in the range of about 0.1 T to about 30 T. For example, some of the experiments that are described herein were performed at 5 T. The radiation for exciting electron spin transitions in the unpaired electron(s) of the polarizing agent at these fields will be in the range of about 2.8 GHz to about 840 GHz. For examples, the radiation in the experiments that are described herein was from a 140 GHz gyrotron.

When studying molten samples (e.g., by liquid-state NMR), the sample may be recycled by freezing the sample, repolarizing the at least one spin half nucleus of the analyte by irradiating the frozen sample with radiation having a frequency that excites electron spin transitions in the biradical, remelting the frozen sample to produce a molten sample, and redetecting nuclear spin transitions in the at least one spin half nucleus of the analyte in the molten sample. This process can be repeated for as many cycles as needed. This can be used, e.g., to signal average NMR signals and thereby further enhance the sensitivity of the NMR experiment. The freezing step can generally be achieved by cooling the sample until it reaches a solid state. In certain embodiments, the sample can be cooled to a temperature of less than about 200 K. For example, the sample may be cooled to a temperature in the range of about 1 K to about 100 K. Some of the experiments that are described herein involved cooling the sample to a temperature of about 90 K. In one embodiment, the freezing step may be completed in less than about 2 minutes, e.g., less than about 1 minute.

In general, once a frozen sample has been polarized according to the present invention it can be optionally melted prior to signal detection using any suitable method. In certain embodiments, this is achieved by exposing the frozen sample to radiation having a wavelength of less than about 100 μm, e.g., in the range of about 0.5 μm and about 50 μm. In one embodiment, the radiation may come from a laser, e.g., a $CO_2$ laser. In another embodiment, the radiation may come from a lamp, e.g., an infra-red lamp. The frozen sample can be exposed to the radiation using an optical fiber. This will typically involve coupling the radiation (e.g., from a laser or lamp) to one end of the fiber, e.g., using a lens. In one embodiment, the sample is within a cylindrical rotor. Advantageously, the rotor can be made of quartz which allows both microwave radiation (e.g., the 140 GHz radiation from a gyrotron) and infra-red radiation (e.g., from a $CO_2$ laser) to reach the sample. We have also found that a quartz rotor does not crack when exposed to multiple freeze-thaw cycles. Finally, the use of a cylindrical rotor enables the sample to be spun during the melting step (and optionally during other steps including the detecting step) which we have found to significantly improve melting homogeneity and time. In the experiments that are described herein we were able to melt samples in less than about 1 second.

In one embodiment, the methods are performed with a biradical having a structure of formula (I) with the proviso that $Q_1$ and $Q_2$ are different when $X_1$ and $X_2$ are —O—. In one embodiment, the biradical has a structure of formula (I) wherein $M_1$ and $M_2$ are, independently, a cyclic or acyclic nitroxide of the formula:

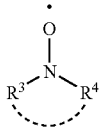

wherein $R^3$ and $R^4$ are, independently, substituted or unsubstituted, cyclic or acyclic aliphatic; substituted or unsubstituted, cyclic or acyclic heteroaliphatic; substituted or unsubstituted aryl; substituted or unsubstituted heteroaryl; wherein

is a group which optionally joins $R^3$ and $R^4$ to form a 5- to 6-membered heterocyclic ring, and with the proviso that each group $R^3$ or $R^4$ does not contain hydrogens alpha to the (N—O.) group;

$Q_1$ corresponds to the formula:

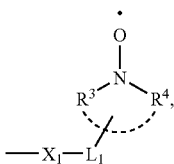

wherein the point of attachment of the group $L_1$-$X_1$ is to either $R^3$, to $R^4$, or to the 5- to 6-membered heterocyclic ring formed by the joining of $R^3$ and $R^4$; and $Q_2$ corresponds to the formula:

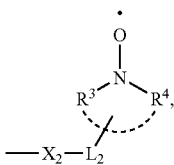

wherein the point of attachment of the group $L_2$-$X_2$ is to either $R^3$, to $R^4$, or to the 5- to 6-membered heterocyclic ring formed by the joining of $R^3$ and $R^4$.

In one embodiment, the biradical has a structure of formula (I) wherein $Q_1$ is a cyclic nitroxide group of the formulae:

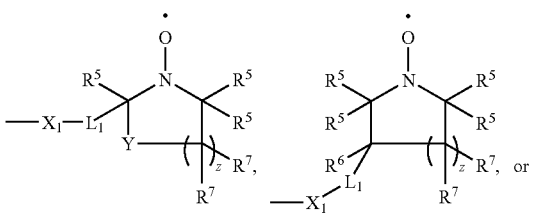

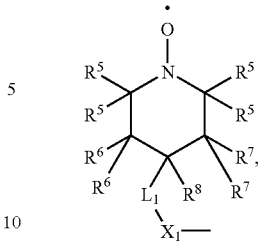

wherein each instance of $R^5$ is independently, substituted or unsubstituted, cyclic or acyclic $C_{1-6}$ aliphatic; substituted or unsubstituted, cyclic or acyclic $C_{1-6}$ heteroaliphatic; substituted or unsubstituted aryl, substituted or unsubstituted heteroaryl, with the proviso that each group $R^5$ does not contain hydrogens alpha to the (N—O·) group;

Y is selected from —O—, —S—, —N($R^2$)—, or —C($R^6$)$_2$—;

$R^2$ is hydrogen, a suitable amino protecting group; substituted or unsubstituted amino; substituted or unsubstituted hydroxyl; substituted or unsubstituted, cyclic or acyclic $C_{1-6}$ aliphatic; substituted or unsubstituted, cyclic or acyclic $C_{1-6}$ heteroaliphatic; substituted or unsubstituted aryl, substituted or unsubstituted heteroaryl, acyl; $C_{1-6}$ alkyl sulfonyl; $C_{1-6}$ alkyl sulfinyl; substituted or unsubstituted aryl sulfinyl; or substituted or unsubstituted aryl sulfonyl;

each $R^6$, $R^7$, and $R^8$ is independently selected from hydrogen, substituted or unsubstituted hydroxyl; substituted or unsubstituted thiol; substituted or unsubstituted amino; nitro; halo; cyano; azido; substituted or unsubstituted, cyclic or acyclic $C_{1-6}$ aliphatic; substituted or unsubstituted, cyclic or acyclic $C_{1-6}$ heteroaliphatic; substituted or unsubstituted aryl, substituted or unsubstituted heteroaryl, acyl; $C_{1-6}$ alkyl sulfonyl; $C_{1-6}$ alkyl sulfinyl; substituted or unsubstituted aryl sulfinyl; or substituted or unsubstituted aryl sulfonyl; and z is 1 or 2.

In one embodiment, the biradical has a structure of formula (I) wherein $Q_2$ is a cyclic nitroxide group of the formulae:

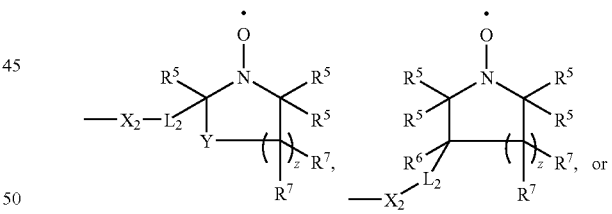

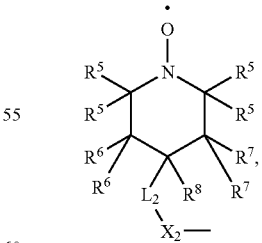

wherein each instance of $R^5$ is independently, substituted or unsubstituted, cyclic or acyclic $C_{1-6}$ aliphatic; substituted or unsubstituted, cyclic or acyclic $C_{1-6}$ heteroaliphatic; substituted or unsubstituted aryl, substituted or unsubstituted heteroaryl, with the proviso that each group $R^5$ does not contain hydrogens alpha to the (N—O·) group;

Y is selected from —O—, —S—, —N(R$^2$)—, or —C(R$^6$)$_2$—;

R$^2$ is hydrogen, a suitable amino protecting group; substituted or unsubstituted amino; substituted or unsubstituted hydroxyl; substituted or unsubstituted, cyclic or acyclic C$_{1-6}$ aliphatic; substituted or unsubstituted, cyclic or acyclic C$_{1-6}$ heteroaliphatic; substituted or unsubstituted aryl, substituted or unsubstituted heteroaryl, acyl; C$_{1-6}$ alkyl sulfonyl; C$_{1-6}$ alkyl sulfinyl; substituted or unsubstituted aryl sulfinyl; or substituted or unsubstituted aryl sulfonyl; each R$^6$, R$^7$, and R$^8$ is independently selected from hydrogen, substituted or unsubstituted hydroxyl; substituted or unsubstituted thiol; substituted or unsubstituted amino; nitro; halo; cyano; azido; substituted or unsubstituted, cyclic or acyclic C$_{1-6}$ aliphatic; substituted or unsubstituted, cyclic or acyclic C$_{1-6}$ heteroaliphatic; substituted or unsubstituted aryl, substituted or unsubstituted heteroaryl, acyl; C$_{1-6}$ alkyl sulfonyl; C$_{1-6}$ alkyl sulfinyl; substituted or unsubstituted aryl sulfinyl; or substituted or unsubstituted aryl sulfonyl; and z is 1 or 2.

In one embodiment, the biradical has a structure of formula (I) wherein Q$_1$ is a cyclic nitroxide group of the formula:

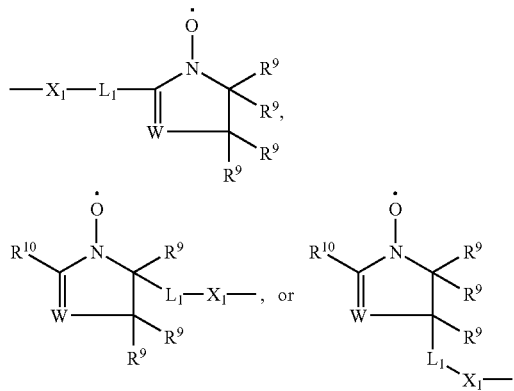

wherein each instance of R$^9$ is, independently, hydrogen, substituted or unsubstituted hydroxyl; substituted or unsubstituted thiol; substituted or unsubstituted amino; nitro; halo; cyano; azido; substituted or unsubstituted, cyclic or acyclic C$_{1-6}$ aliphatic; substituted or unsubstituted, cyclic or acyclic C$_{1-6}$ heteroaliphatic; substituted or unsubstituted aryl, substituted or unsubstituted heteroaryl, acyl; C$_{1-6}$ alkyl sulfonyl; C$_{1-6}$ alkyl sulfinyl; substituted or unsubstituted aryl sulfinyl; or substituted or unsubstituted aryl sulfonyl;

R$^{10}$ is hydrogen, substituted or unsubstituted, cyclic or acyclic C$_{1-6}$ aliphatic; substituted or unsubstituted, cyclic or acyclic C$_{1-6}$ heteroaliphatic; substituted or unsubstituted aryl, or substituted or unsubstituted heteroaryl; and W is N or $\oplus$N—O$\ominus$.

In one embodiment, the biradical has a structure of formula (I) wherein Q$_2$ is a cyclic nitroxide group of the formula:

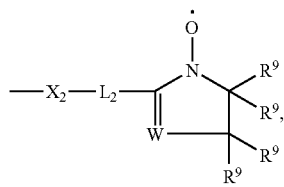

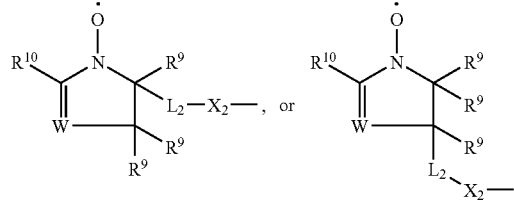

wherein each instance of R$^9$ is, independently, hydrogen, substituted or unsubstituted hydroxyl; substituted or unsubstituted thiol; substituted or unsubstituted amino; nitro; halo; cyano; azido; substituted or unsubstituted, cyclic or acyclic C$_{1-6}$ aliphatic; substituted or unsubstituted, cyclic or acyclic C$_{1-6}$ heteroaliphatic; substituted or unsubstituted aryl, substituted or unsubstituted heteroaryl, acyl; C$_{1-6}$ alkyl sulfonyl; C$_{1-6}$ alkyl sulfinyl; substituted or unsubstituted aryl sulfinyl; or substituted or unsubstituted aryl sulfonyl;

R$^{10}$ is hydrogen, substituted or unsubstituted, cyclic or acyclic C$_{1-6}$ aliphatic; substituted or unsubstituted, cyclic or acyclic C$_{1-6}$ heteroaliphatic; substituted or unsubstituted aryl, or substituted or unsubstituted heteroaryl; and W is N or $\oplus$N—O$\ominus$.

In one embodiment, the biradical has a structure of formula (I) wherein L$_1$ and L$_2$ are independently, a single bond or —CH$_2$—.

In one embodiment, the biradical has a structure of formula (I) wherein X$_1$ is —O—, and X$_2$ is —N(R$^2$)—. In one such embodiment, R$^2$ is hydrogen.

In one embodiment, the biradical has a structure of formula (II):

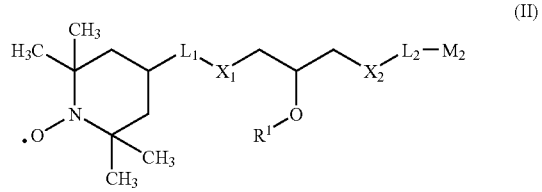

wherein each group is defined as above for formula (I).

In one embodiment, the biradical has a structure of formula (II) wherein X$_1$ is —O—.

In one embodiment, the biradical has a structure of formula (IIA):

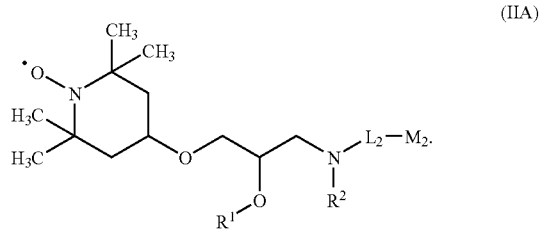

In one embodiment, the biradical is selected from the group consisting of biradicals of formulae:

(IIB)

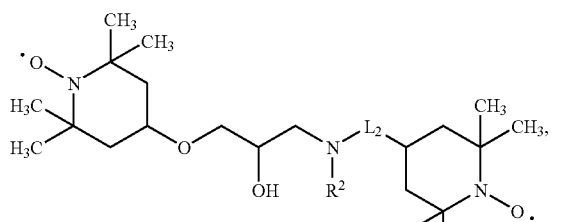

(IIC)

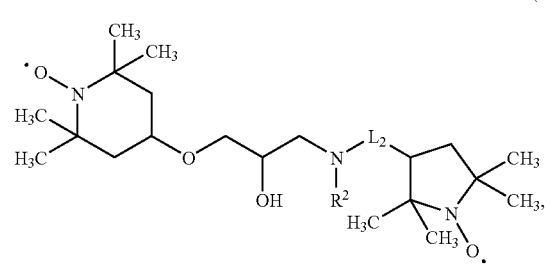

(IID)

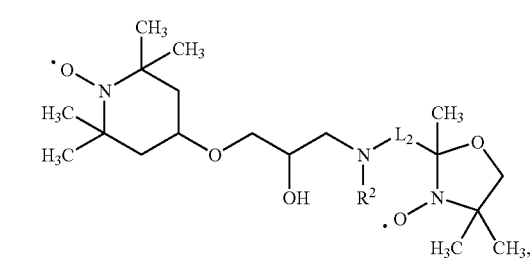

(IIE)

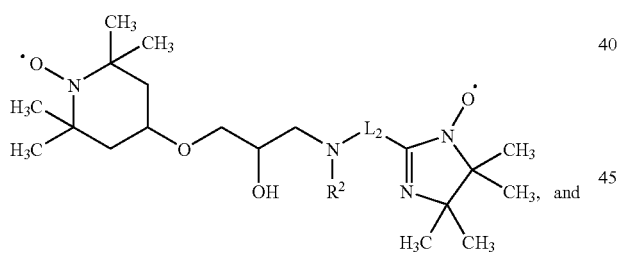

(IIF)

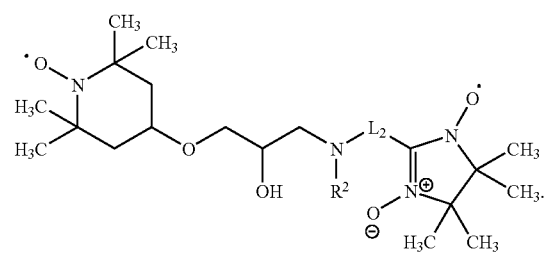

In one embodiment, the biradical is 1-(TEMPO-4-oxy)-3-(TEMPO-4-amino)-propan-2-ol.

In another aspect, the present invention provides any one of the aforementioned biradicals with the proviso that $Q_1$ and $Q_2$ are different when $X_1$ and $X_2$ are —O—.

In yet another aspect, the present invention provides a method of making biradicals having the structure of formula (IA):

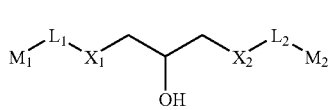

(IA)

wherein $X_1$ and $X_2$ are independently selected from —O—, —S—, or —N($R^2$)—, wherein $R^2$ is hydrogen, a suitable amino protecting group; substituted or unsubstituted amino; substituted or unsubstituted hydroxyl; substituted or unsubstituted, cyclic or acyclic $C_{1-6}$ aliphatic; substituted or unsubstituted; cyclic or acyclic $C_{1-6}$ heteroaliphatic; substituted or unsubstituted aryl, substituted or unsubstituted heteroaryl, acyl; $C_{1-6}$ alkyl sulfonyl; $C_{1-6}$ alkyl sulfinyl; substituted or unsubstituted aryl sulfinyl; or substituted or unsubstituted aryl sulfonyl;

$L_1$ and $L_2$ are independently selected from a direct bond; substituted or unsubstituted, cyclic or acyclic $C_{1-6}$ aliphatic; or substituted or unsubstituted, cyclic or acyclic $C_{1-6}$ heteroaliphatic; and $M_1$ and $M_2$ are, independently, a substituted or unsubstituted, cyclic or acyclic nitroxide; the method comprising steps of:

(i) reacting a compound of formula:

with a compound of formula:

wherein $LG_1$ is a suitable leaving group, to provide a compound of formula:

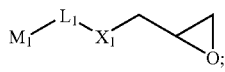

and then (ii) reacting the compound of formula:

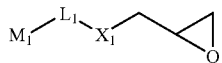

with a compound of formula:

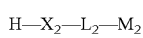

to provide a biradical of formula (IA).

In one embodiment, $LG_1$ is –I, —Br, or —Cl. In another embodiment, $LG_1$ is —Cl. In one embodiment, $X_1$ is —O—. In one embodiment, $X_2$ is —NH—. In one embodiment, the method may be used to make 1-(TEMPO-4-oxy)-3-(TEMPO-4-amino)-propan-2-ol (i.e., TOTAPOL).

EXAMPLES

Example 1

Synthesis of TOTAPOL 1-(TEMPO-4-oxy)-3-(TEMPO-4-amino)-propan-2-ol (TOTAPOL) was prepared according to the two-step reaction illustrated in Scheme 1 below. The conditions were: (a) epichlorohydrin, tetrabutylammonium hydrogensulfate, 50% w/w $NaOH_{(aq)}$, room temperature and (b) $LiClO_4$, $CH_3CN$, room temperature.

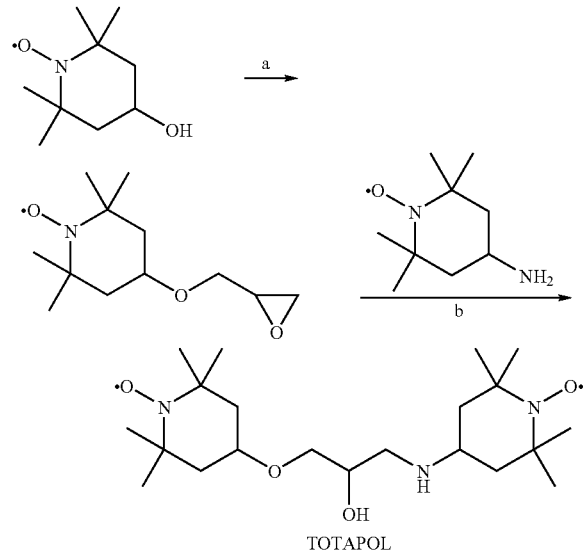

Scheme 1

TOTAPOL

Figure 7:
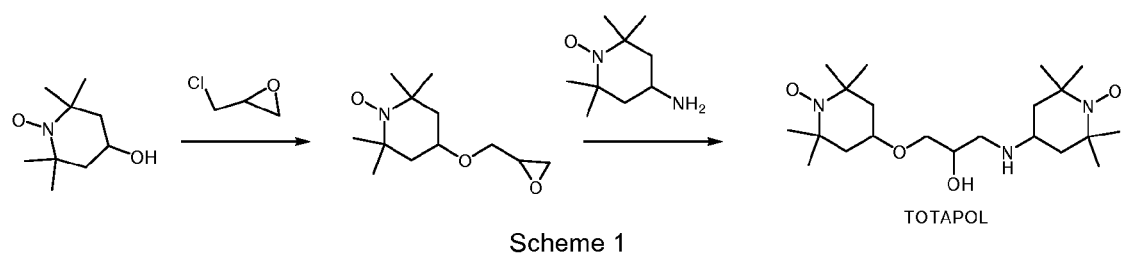
FIG. 7 shows an exemplary method of making TOTAPOL (Scheme 1).

Note that the molecule is an asymmetric biradical with an ether and a secondary amino linkage in contrast to the symmetrical bis-TEMPO-ethylene oxide biradicals that we described previously[23]. Some exemplary variations on Scheme 1 are illustrated in FIG. 7.

General Experimental Conditions.

4-hydroxy-TEMPO and 4-amino-TEMPO were purchased from Aldrich (free radical ≧97.0%) and used without further purification. Anhydrous CH3CN was purchased from Aldrich as a Sure-Seal bottle. All other chemicals were of reagent grade and used as received. For NMR analysis, TEMPO radicals were reduced to N-hydroxy compounds by ascorbic acid in methanol. NMR spectra were recorded on a Bruker Advance-400 or Varian Mercury-300 spectrometer, and chemical shift were referenced to residual solvent peaks. IR spectra were obtained on a Nicolet 8700 FT-IR spectrometer, in which sample was drop-casted on a KBr disc. High-resolution mass spectra were obtained on a Bruker Daltonics APEX II 3T FT-ICRMS.

4-(2,3-epoxy-propoxy)-2,2,6,6-tetramethyl-1-piperidinyloxy [4-(2,3-epoxy-propoxy)-TEMPO]

In a 100 mL round-bottom flask equipped with a stirring bar were combined tetrabutylammonium hydrogensulfate (0.136 g, 4 mol %), 50% w/w aqueous NaOH (10 mL), and epichlorohydrin (3.91 mL, 50 mmol). To the mixture was added 4-hydroxy-TEMPO in portions and the mixture was stirred overnight at room temperature. It was then poured into water and extracted with ethyl acetate. The organic layer was washed with brine, dried over MgSO4, and evaporated under reduced pressure. The resulting crude product was purified by column chromatography (dichloromethane, methanol), providing a quantitative yield of red, viscous oil. $^1$H-NMR (300 MHz, DMSO-$d_6$) δ: 7.12 (bs, 1H), 3.69 (dd, 1H, J=11, 2.7 Hz), 3.60 (m, 1H), 3.24 (dd, 1H, J=11, 6.6 Hz), 3.04 (m, 1H), 2.70 (pseudo-t, 1H, J=5.1 Hz), 2.52 (dd, 1H, J=5.1, 2.7 Hz), 1.86 (dd, 2H, J=12, 3.6 Hz), 1.24 (pseudo-t, 2H, J=11 Hz), 1.05 (d, 12H, J=11 Hz).

1-(2,2,6,6-tetramethyl-1-oxy-4-piperidinyl)oxy-3-(2,2,6,6-tetramethyl-1-oxy-4-piperidinyl)amino-propan-2-ol [1-(TEMPO-4-oxy)-3-(TEMPO-4-amino)-propan-2-ol] (TOTAPOL)

In a 100 mL round-bottom flask equipped with a stirring bar were combined 4-oxyranylmethoxy-TEMPO (1.62 g, 7 mmol), LiClO4 (0.745 mg, 7 mmol), and 10 mL of anhydrous $CH_3CN$ under Ar. To the mixture was added a $CH_3CN$ (3 mL) solution of 4-amino-TEMPO (1.20 g, 7 mmol) and the mixture was stirred overnight at room temperature. Most of the solvent was evaporated under reduced pressure, and the crude product was purified by column chromatography (dichloromethane, methanol). Yield: 1.98 g of orange-red solid. $^1$H-NMR (400 MHz, DMSO-$d_6$) δ: 7.31 (bs, 1H), 7.15 (bs, 1H), 4.57 (bs, 1H), 3.93 (m, 1H), 3.69 (m, 1H), 3.57 (m, 1H), 3.41 (m, 2H), 3.34 (m, 1H), 3.01 (pseudo-d, 1H, J=11 Hz), 2.80 (m, 1H), 1.96 (m, 2H), 1.86 (m, 2H), 1.52 (m, 2H), 1.23 (pseudo-t, 2H, J=11 Hz), 1.04 (dd, 24H, J=17, 3.9 Hz). HR-MS (ESI): calcd for $C_{21}H_{41}N_3O_4$ [M +H]$^+$, 400.3170; found, 400.3161.

Example 2

EPR Experiments

For 9 GHz solution EPR experiments, the samples consisted of a capillary containing ~10 μL's of 0.5 mM TOTAPOL in absolute ethanol. In order to increase the resolution of powder EPR spectra from frozen solutions, TOTAPOL was synthesized with $^{15}$N, $^2$H-labeled TEMPO's (CDN Isotope, Quebec, Canada). Samples for the X-band experiments were typically 60 μL of 0.5 mM $^{15}$N, $^2$H-TOTAPOL in the glass forming solvent $d_6$-DMSO/$D_2$O (6:4 w/w) in a 4 mm O.D. quartz tube. 9 GHz CW EPR spectra were recorded with a Bruker EMX spectrometer with the sample immersed in liquid nitrogen (77 K) in a finger dewar, (Wilmad WG-819—B-Q). Samples for 140 GHz experiments consisted of 0.4 μL of TOTAPOL in $d_6$-DMSO/$D_2$O (6:4 w/w) contained in a quartz capillary immersed in a helium cryostat (Oxford Instruments). 140 GHz spectra were recorded with echo detected experiments using a custom designed spectrometer[24]. The rigid-limit for EPR spectra of TOTAPOL is reached below 100 K in the glass forming DMSO/$D_2$O mixture; thus, the 20 K and 100 K temperatures chosen for the above EPR experiments are sufficient for observing rigid limit EPR spectra.

The EPR spectra of flexible biradicals such as BTnE, two TEMPO's tethered by "n" ethylene glycol units[23], usually have two additional peaks yielding a quintet spectrum with the lines spaced at about half the normal 16.7 G $^{14}$N hyperfine splitting observed in TEMPO. This five-line solution EPR spectrum is a result of proximity of the two TEMPO radicals and arises when the average J-coupling (exchange integral) is ≧10 times stronger than the hyperfine coupling[41]. This phenomenon is illustrated in FIGS. 1a-b which shows the solution EPR spectra of 4-amino TEMPO and the biradical BT2E. There are three lines present in the TEMPO spectrum, but in the BT2E spectrum there are two additional lines arising from the strong J-coupling between the electrons. In contrast, the spectrum of TOTAPOL (FIG. 1c) shows that the two additional biradical lines are broadened into the baseline due to the short tether (—O—CH$_2$—CHOH—CH$_2$—NH—) that restricts the proximity of two TEMPO moieties.

Moreover, the EPR spectrum of 0.5 mM TOTAPOL in d$_6$-DMSO/D$_2$O (6:4 w/w) glassforming solution at 77 K (FIG. 1f) reveals a significantly broadened lineshape with a resolved dipolar splitting at 3360 G. Note for comparison that neither the broadening or the splitting are present in the spectrum of frozen monomeric TEMPO at 1 mM (FIG. 1d). For TOTAPOL, the 8 Gauss splitting is observed at $g_{zz}$[42] at both 9 GHz (FIG. 1f) and 140 GHz (FIG. 1i) arises from an intra molecular electron-electron dipolar coupling. As a comparison, the powder EPR spectrum of BT2E reveals a broadened feature (FIGS. 1e, 1h) at this field position. Simulations of the powder EPR lineshapes yielded similar electron-electron distances (~12.8 Å) for both BT2E and TOTAPOL, even though the involved molecular tethers are composed of different numbers of atoms. Since an electron-electron dipolar splitting is observed in the powder EPR spectra (FIGS. 1f and 1i), we surmise that the conformational flexibility of the tether in TOTAPOL may be decreased by its short length. In contrast, the longer and conformationally more flexible tether in BT2E probably permits a distribution of orientations of the g-tensors of the two TEMPO moieties and thereby transforms the dipolar splitting visible at 3360 G to a broad peak (FIG. 1e). A similar dipolar splitting and broadening are present in the 140 GHz biradical spectra (FIGS. 1h, 1i), where inhomogeneous broadening due to the larger g-anisotropy dominates the lineshape. Both the solution and solid-state EPR spectra of TOTAPOL provide information on the distance between the two TEMPO moieties and a detailed analysis of these lineshapes will be the subject of a future publication.

Example 3

DNP Enhanced NMR Experiments with TOTAPOL

Solutions for the DNP/NMR experiments—2 M $^{13}$C-urea or 0.15 M U—$^{13}$C—$^{15}$N-proline—were prepared in d$_6$-DMSO/D$_2$O/H$_2$O (60:34:6 w/w) or d$_8$-glycerol/D$_2$O/H$_2$O (60:32:8 w/w), and doped with 5 mM TOTAPOL (10 mM electron spins). The reduced $^1$H concentration was required to optimize the signal enhancements. DNP experiments using TOTAPOL as a polarizing agent were performed on a custom designed DNP/NMR spectrometer and triple-resonance (e$^-$, $^1$H and $^{13}$C/$^{15}$N) cryogenic (90 K) MAS probe[31] operating at 5 T (140 GHz EPR and 211 MHz $^1$H NMR). The enhanced $^1$H polarization developed by the microwave irradiation was detected indirectly via observation of the cross-polarized (CP) $^{13}$C signals. The 140 GHz microwaves were generated by a gyrotron, a vacuum electron device capable of producing high power (>10 W) millimeter waves[26]. In certain embodiments, sapphire, rather than zirconia, rotors are preferred for the DNP experiments since they transmit microwaves with ~30% less attenuation. In addition, the 5 T magnet has a superconducting sweep coil used to vary the field by ±750 G for EPR and DNP experiments, and that facilitates locating the maximum and minimum in the DNP enhancement curve from its field dependence.

Figure 2:
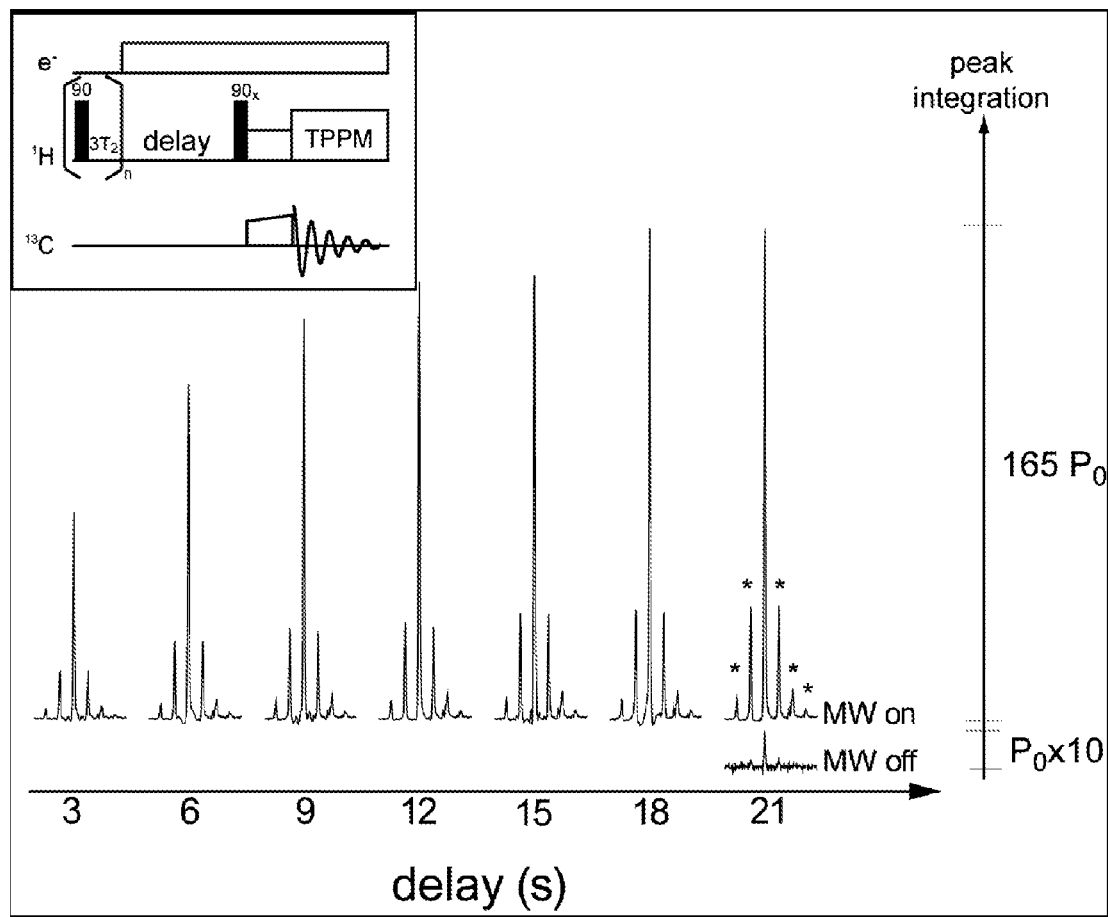
FIG. 2 is an illustration of the growth of the nuclear polarization as a result of microwave irradiation. Integration of the spectral intensities with and without irradiation yields a $^1$H enhancement of ~165 measured indirectly through $^{13}$C CP signal using the pulse sequence shown in the inset. The measurements were performed on a sample of 5 mM TOTAPOL and 2 M $^{13}$C-urea in d$_6$-DMSO/D$_2$O/H$_2$O (60:34:6 w/w) at 90 K, 5 T and $\omega_r/2\pi$=3.5 kHz MAS (giving rise to side bands as asterisks mark). The time constant associated for the growth is 5.5 s, approximately the nuclear T$_1$ of the sample.

The pulse sequence for DNP enhanced $^{13}$C-CPMAS NMR experiments is shown in the inset of FIG. 2. The $^1$H polarization is initially saturated by a series of 90° pulses followed by a delay of 3 T$_2$. Next, the microwave irradiation is applied to dynamically polarize the $^1$H's, or, in the absence of microwaves, the thermal equilibrium polarization develops. Finally, the $^1$H polarization is transferred to $^{13}$C via cross polarization and observed in the presence of TPPM decoupling[43]. The Fourier transforms of the FIDs are shown (FIG. 2) as a series of spectra with various microwave irradiation periods. The rotational side bands spaced at $\omega_r/2\pi$=3.5 kHz, are marked by asterisks. The enhanced signals (microwaves on) developed with a time constant of ~5.5 s, which is similar to the proton T$_1$. Thus, the enhancement factor is determined by comparing the saturated NMR signals (after 21 s delay) with and without microwaves, and for TOTAPOL is ~165±20 for the $^1$H polarization. Note that the error for the enhancement factor is determined primarily by the uncertainty in measuring the intensity of the un-enhanced NMR signal.

Figure 3:
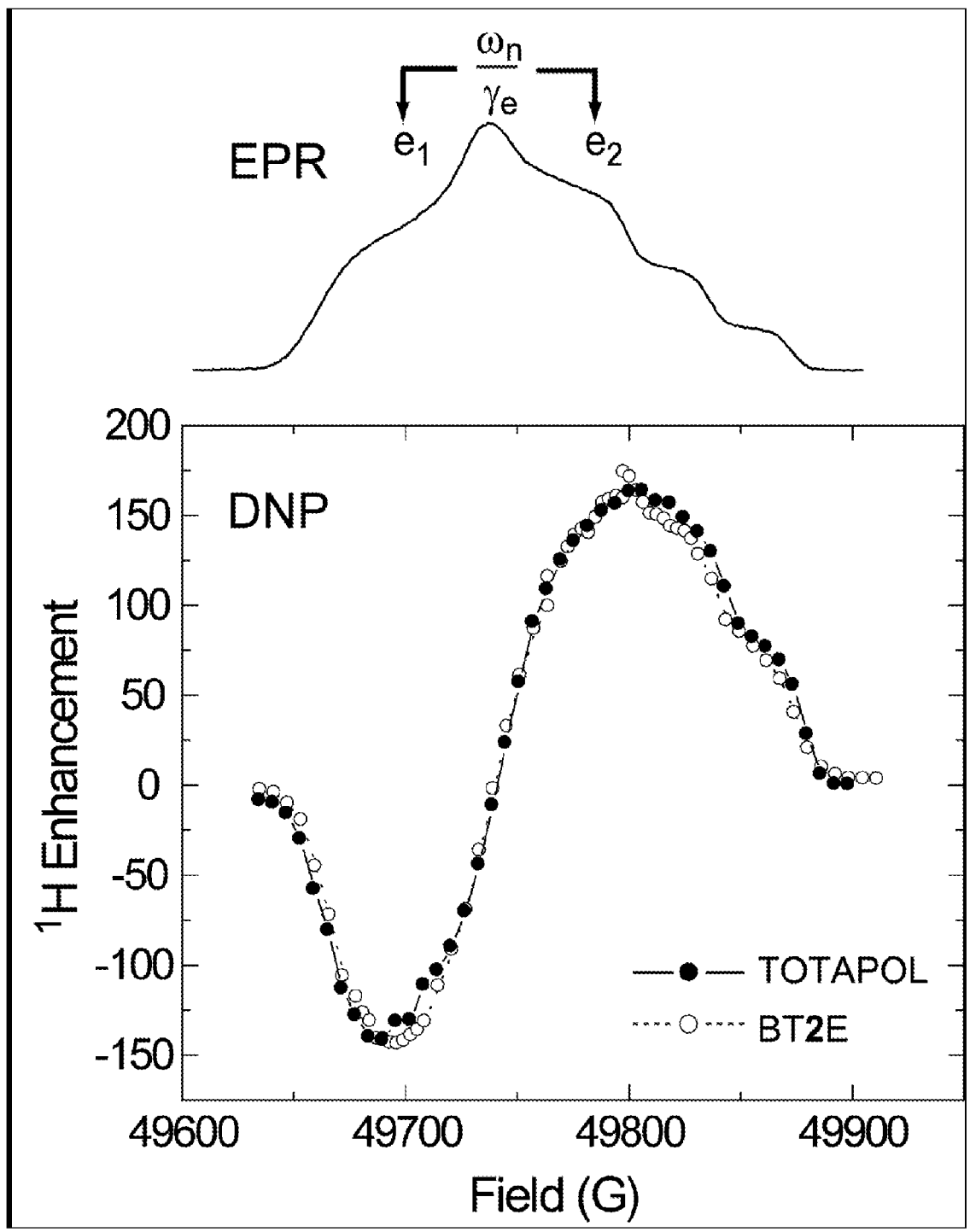
FIG. 3 (top) shows the EPR absorption of TOTAPOL measured on a 140 GHz spectrometer. The linewidth is much greater than the $^1$H Larmor frequency ($\omega_n/2\pi$) and therefore can encompass two coupled electron spins with the correct EPR frequency separation, $\omega_n$, required for the cross effect.

In the top half of FIG. 3 we show the EPR absorption of TOTAPOL recorded at 140 GHz/5 T. This inhomogeneous lineshape supports the cross effect mechanism in which two dipole-coupled electrons, separated by $\omega_n/2\pi$ in the EPR spectrum, execute a threespin electron-electron-nucleus method involving the mutual flip of an electron and a second electron separated by $\omega_n/2\pi$ and a nuclear spin. The energy difference matches the nuclear Larmor frequency and results in nuclear spin flips that generate the enhanced nuclear polarization. The correct frequency separation of the two electrons is provided by the fact that the two TEMPO moieties have relative g-tensor orientations that satisfy the correct matching condition $\omega_{2e}-\omega_{1e}=\omega_n$. The field dependence of the DNP enhancement with TOTAPOL is shown in the bottom half of FIG. 3, together with the enhancement curve of BT2E. The enhancement curves generally resemble a sinusoidal shape with features of the EPR absorptive spectrum visible—the $^{14}$N hyperfine coupling. The maximum and minimum enhancements are 165 and −140 separated by 107 G (~300 MHz). The enhancement curves can be compared with the EPR lineshape in the top half of FIG. 3. Although the TOTAPOL chain is shorter than in BT2E and probably less flexible, we nevertheless observe essentially the same shape for the enhancement curve for each case. The shape and amplitude of the two curves depend on the average interelectron separation and relative orientations of the two g-tensors which we surmise must be on average very nearly the same in the two molecules.

Figure 4:
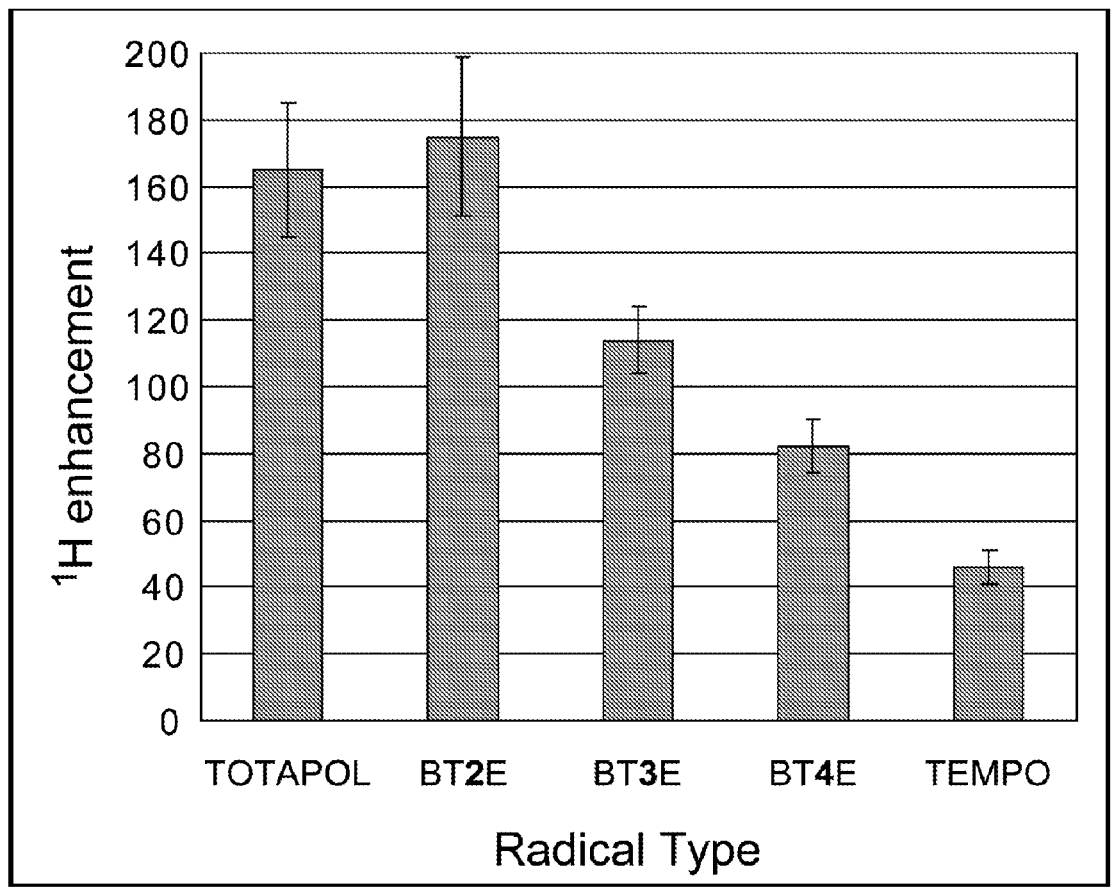
FIG. 4 shows a histogram of DNP enhancements (with error bars) from the TOTAPOL and a series of BTnE biradicals (for n=2, 3 and 4, referring to the structures in FIG. 1). TOTAPOL yielded an enhancement close to that by BT2E. This may suggest that the optimal inter-radical distance have been approximated within BT2E.

FIG. 4 shows a comparison of the enhancement from TOTAPOL with those from BTnE (n=2, 3, 4) series of biradicals. Reducing the number of atoms separating the two TEMPO moieties increases the electron-electron dipolar interaction and the observed enhancement. As the DNP enhancement strongly depends on the electron-electron dipolar interaction, it appears to be optimized for BT2E and TOTAPOL at ~165. That the shorter tether in TOTAPOL (five as opposed to seven atoms between the rings of TEMPO) does not yield larger DNP enhancement may be due to the fact that: (1) BT2E has a flexible linker and may have an average distance similar to TOTAPOL or (2) the relative orientation of the g-tensors in BT2E may be nearer to an optimum. A measurement of the electron-electron distances and g-tensor orientations should provide an answer.

Figure 5:
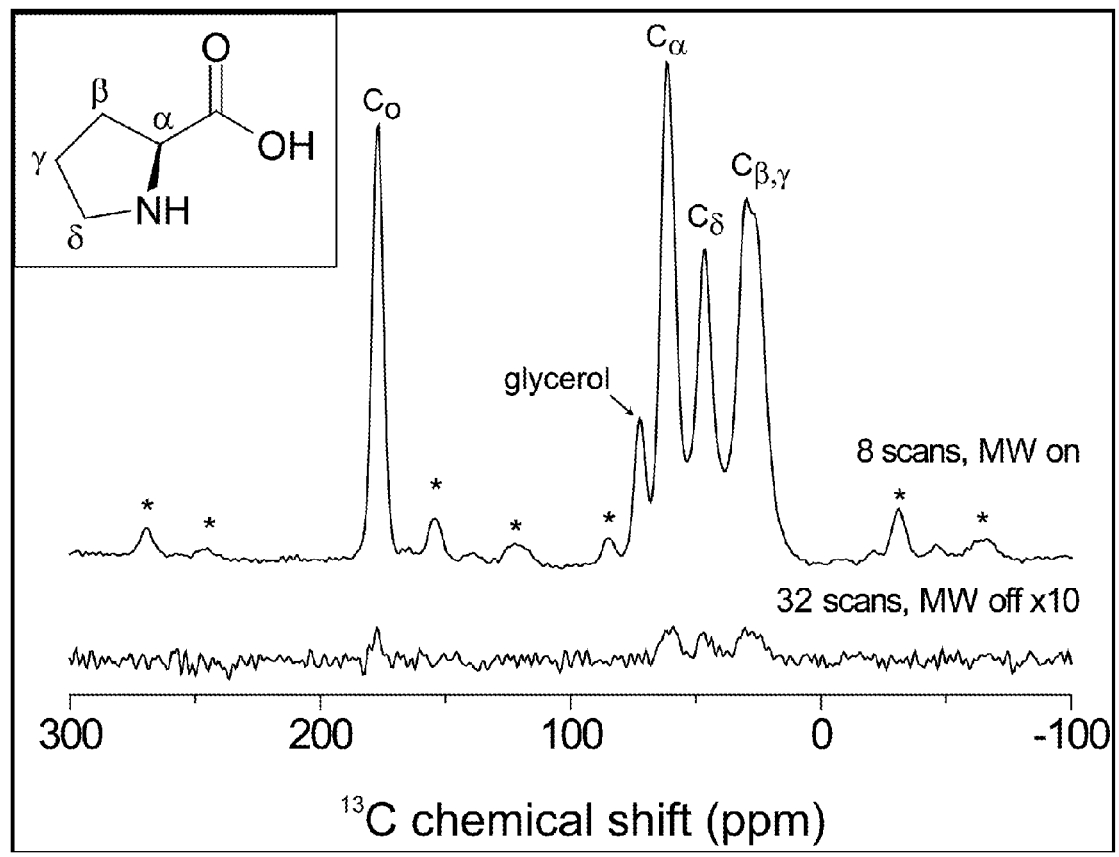
FIG. 5 shows the DNP enhanced spectrum of a 25 μL sample of 150 mM proline solution doped with 5 mM TOTAPOL. An enhancement of 160 was observed in the experiment with 18 s microwave irradiation. The sample was prepared in $d_8$-glycerol/$D_2O$/$H_2O$ (60:32:8 w/w) and the spectra were recorded with $\omega_r/2\pi$=4.8 kHz MAS at 90 K and 5 T. The spectrum is assigned according to the structure of proline shown in the inset. The rotational sidebands are marked by asterisks.
Figure 6:
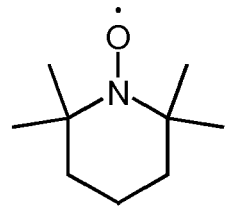
FIG. 6 shows some exemplary nitroxide radicals, methods for synthesizing these and some commercially available derivatives.
Figure 6:
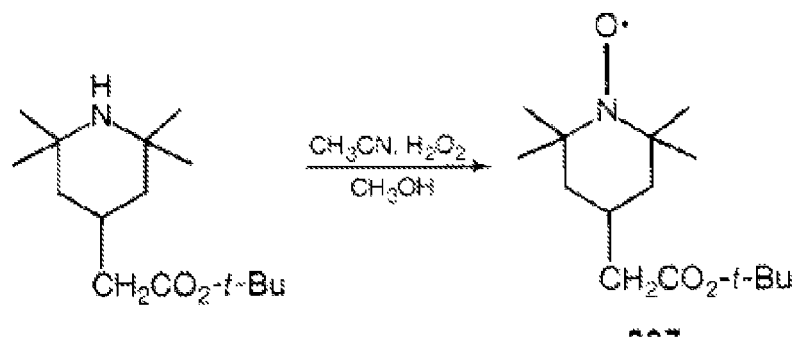
Figure 6:
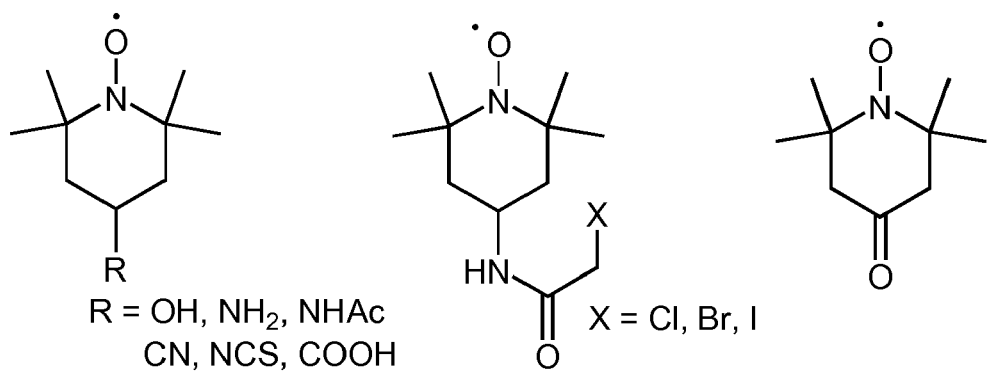
Figure 6:
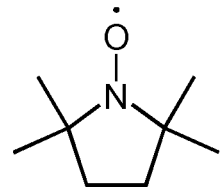
Figure 6:
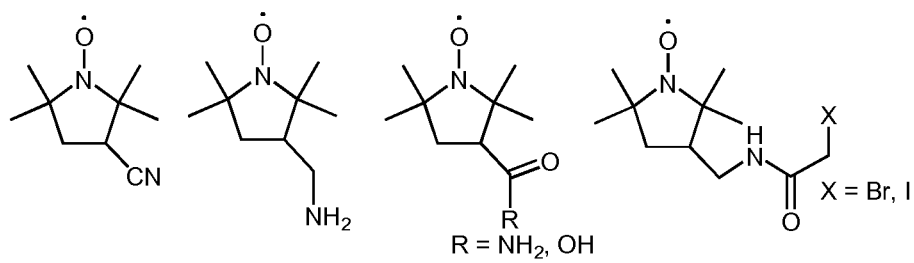
Figure 6:
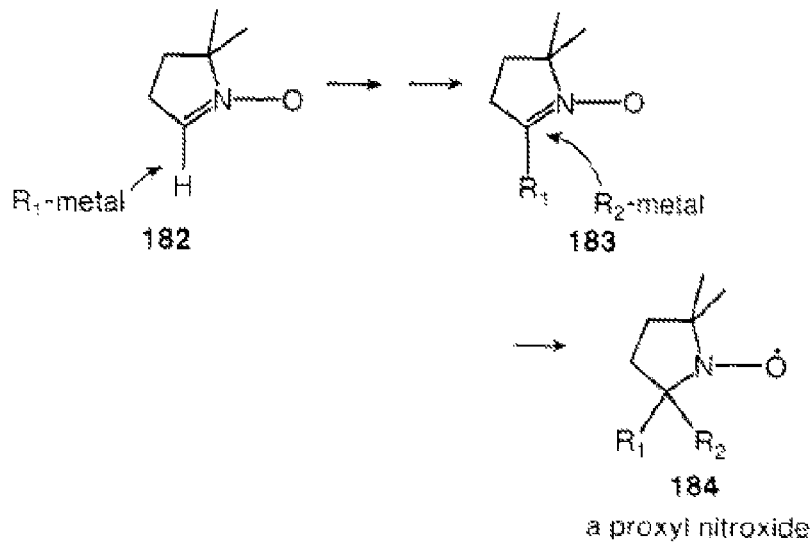
Figure 6:
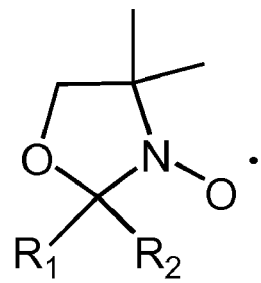
Figure 6:
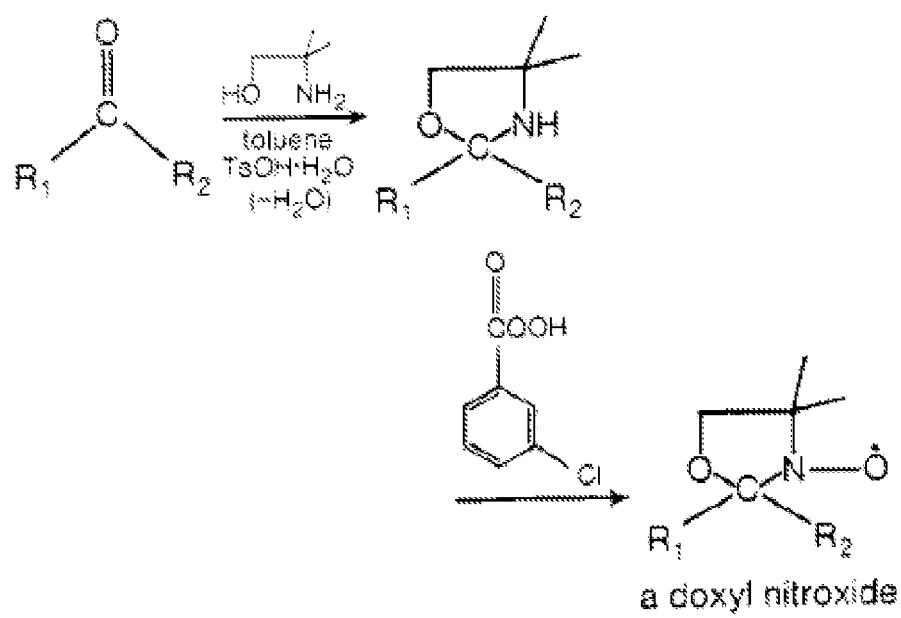
Figure 6:
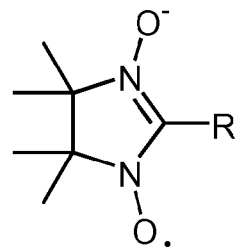
Figure 6:
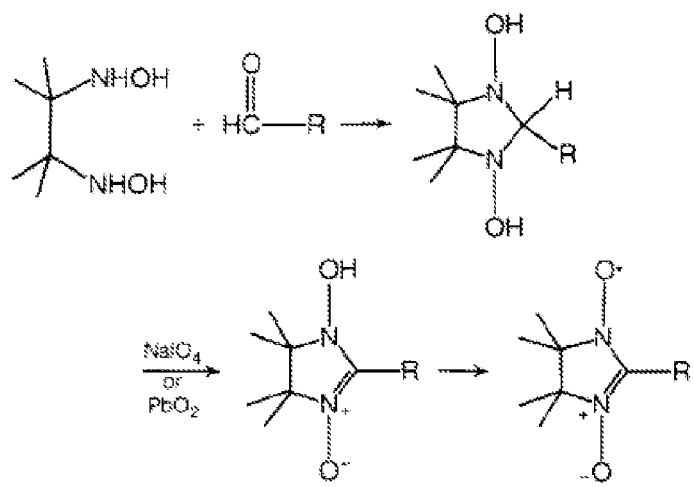
Figure 6:
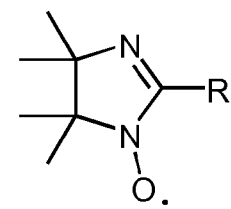
Figure 6:
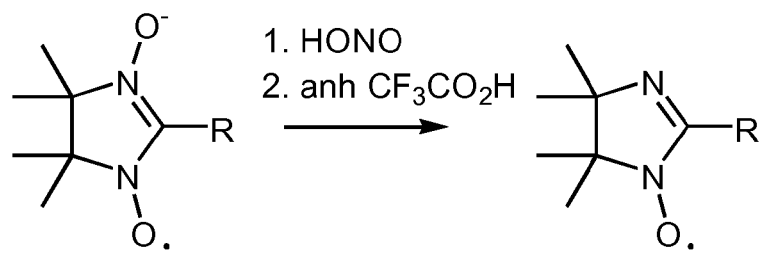
Figure 6:
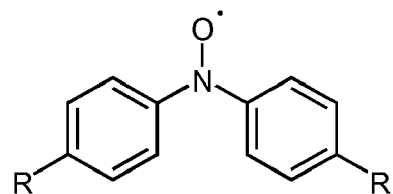
Figure 6:
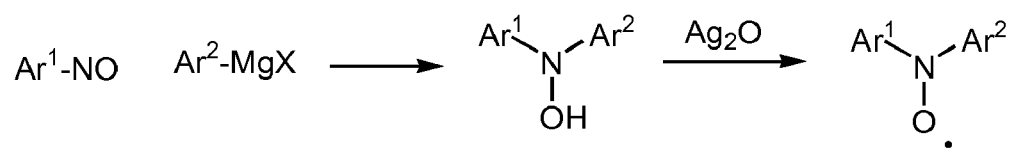

As noted, TOTAPOL is soluble in water due to the —OH group on the central carbon of the tethering chain and the —NH— linkage of the TEMPO moiety. Further, TOTAPOL is soluble in 200 mM salt, solvent conditions that are common in preparation of a protein samples, and it is stable in glycerol/water (6:4 w/w) at −10 °C. for months. In contrast, BT2E is insoluble in all of these media. To illustrate the utility of TOTAPOL in these circumstances we show in FIG. 5 a DNP-enhanced high-resolution $^{13}$C-NMR spectrum of 150 mM proline in d$_8$-glycerol/D$_2$O/H$_2$O (60:32:8 w/w) which exhibits an enhancement of 160 using 5 mM TOTAPOL at 90 K and 5 T. In addition, we have used TOTAPOL to polarize samples of membrane proteins such as bacteriorhosopsin[44, 45], amyloid peptide (e.g., GNNQQNY) nanocrystals[46, 47], and microcrystals of soluble proteins[48-50] so it appears to be compatible with a wide variety of different systems.

EQUIVALENTS

The section headings used herein are for organizational purposes only and are not to be construed as limiting the subject matter described in any way.

While the present invention has been described in conjunction with various embodiments and examples, it is not intended that the present invention be limited to such embodiments or examples. On the contrary, the present invention encompasses various alternatives, modifications, and equivalents, as will be appreciated by those of skill in the art.

While the present invention has been particularly shown and described with reference to specific illustrative embodiments, it should be understood that various changes in form and detail may be made without departing from the spirit and scope of the present invention. Therefore, all embodiments that come within the scope and spirit of the present invention, and equivalents thereto, are intended to be claimed.

REFERENCES (1) Hall, D. A.; Maus, D. C.; Gerfen, G. J.; Inati, S. J.; Becerra, L. R.; Dahlquist, F. W.; Griffin, R. G. *Science* 1997, 276, 930-932.
(2) Hu, K.-N.; Yu, H.-h.; Swager, T. M.; Griffin, R. G. *J. Am. Chem. Soc.* 2004, 126, 10844-10845.
(3) Gerfen, G. J.; Becerra, L. R.; Hall, D. A.; Griffin, R. G.: Temkin, R. J.; Singel, D. J. *J. Chem. Phys.* 1995, 102, 9494-9497.
(4) Becerra, L. R.; Gerfen, G. J.; Temkin, R. J.; Singel, D. J.; Griffin, R. G. *Phys. Rev. Lett.* 1993, 71, 3561-3564.
(5) Bajaj, V. S.; Farrar, C. T.; Mastovsky, I.; Vieregg, J.; Bryant, J.; Elena, B.; Kreischer, K. E.; Temkin, R. J.; Griffin R. G. *J. Magn. Reson.* 2003, 160, 85-90.
(6) Farrar, C. T.; Hall, D. A.; Gerfen, G. J.; Rosay, M.; Ardenkjaer-Larsen, J. H.; Griffin, R. G. *J. Magn. Reson.* 2000, 144, 134-141.
(7) Rosay, M.; Zeri, A. C.; Astrof, N. S.; Opella, S. J.; Herzfeld, J.; Griffin, R. G., *J. Am. Chem. Soc.* 2001,123, 1010-1011.
(8) Rosay, M.; Lansing, J. C.; Haddad, K. C.; Bachovchin, W. W.; Herzfeld, J.; Temkin, R. J.; Griffin, R. G. *J. Am. Chem. Soc.* 2003, 125, 13626-13627.
(9) Van Der Wel, P.; Hu, K.-N.; Lewandowski, J.; Griffin, R. G. in preparation.
(10) Duckett, S. B.; Sleigh, C. J. *Prog. Nucl. Magn. Reson. Spectrosc.* 1999, 34, 71-92
(11) Natterer, J.; Bargon, J. *Prog. Nucl. Magn. Reson. Spectrosc.* 1997, 31, 293-315.
(12) Navon, G.; Song. Y. Q.; Room, T.; Appelt, S.; Taylor, R. E.; Pines, A. *Science* 1996, 271, 1848-1851.
(13) Fitzgerald, R. J.; Sauer, K. L.; Happer, W. *Chem. Phys. Lett.* 1998, 284, 87-92.
(14) Cherubini, A.; Payne, G. S.; Leach, M. O.; Bifone, A. *Chem. Phys. Lett.* 2003, 371, 640-644.
(15) Pavloskaya, G. E.; Cleveland, Z. I.; Stupic, K. F.; Basaraba, R. J.; Meersmann, T. *Proc. Natl. Acad. Sci. U.S.A.* 2005, 102, 18275-18279.
(16) Goto, A.; Hashi, K.; Shimizu, T.; Miyabe, R.; Wen, X. G.; Ohki, S.; Machida, S.; Iijima, T.; Kido, G. *Physical Review B* 2004, 69.
(17) Barrett, S. E.; Tycko, R.; Pfeiffer, L. N.; West, K. W. *Phys. Rev. Lett.* 1994, 72, 1368-1371.
(18) Michal, C. A.; Tycko, R. *Phys. Rev. Lett.* 1998, 81, 3988-3991.
(19) Zysmilich, M. G.; McDermott, A. *J. Am. Chem. Soc.* 1996, 118, 5867-5873.
(20) Polenova, T.; McDermott, A. E. *J. Phys. Chem. B* 1999, 103, 535-548
(21) Prakash, S.; Alia; Gast, P.; deGroot, H. J. M.; Jeschke, G.; Matysik, J *J. Am. Chem. Soc.* 2005, 127, 14290-14298.
(22) Goez, M.; Mok, K. H.; Hore, P. J. *J. Magn. Reson.* 2005, 177, 236-246.
(23) Hu, K.-N.; Yu, H.-h.; Swager, T. M.; Griffin, R. G. *J. Am. Chem. Soc.* 2004, 126, 10844-10845.
(24) Becerra, L. R.; Gerfen, G. J.; Bellew, B. F.; Bryant, J. A.; Hall, D. A.; Inati, S. J.; Weber, R. T.; Un, S.; Prisner, T. F.; McDermott, A. E.; Fishbein, K. W.; Kreischer, K. E.; Temkin, R. J.; Singel, D. J.; Griffin, R. G. *J. Magn. Reson. Ser. A* 1995, 117, 28-40.
(25) Becerra, L. R.; Gerfen, G. J.; Temkin, R. J.; Singel, D. J.; Griffin, R. G. *Phys. Rev. Lett.* 1993, 71, 3561-3564.
(26) Joye, C. D.; Griffin, R. G.; Hornstein, M. K.; Hu, K.-N.; Kreischer, K. E.; Rosay, M.; Shapiro, M. A.; Sirigiri, J. R.; Temkin, R. J.; Woskov, P. P. *IEEE Special Issue on High Power Microwave Generation* 2006, in press.
(27) Hornstein, M. K.; Bajaj, V. S.; Griffin, R. G.; Kreischer, K. E.; Mastovsky, I.; Shapiro, M. A.; Sirigiri, J. R.; Temkin, R. J. *IEEE Trans. Electron Devices* 2005, 52, 798-807.
(28) Wind, R. A.; Duijvestijn, M. J.; Vanderlugt, C.; Manenschijn, A.; Vriend, J. *Prog. Nucl. Magn. Reson. Spectrosc.* 1985, 17, 33-67.
(29) Singel, D. J.; Seidel, H.; Kendrick, R. D.; Yannoni, C. S. *J. Magn. Reson.* 1989, 81,145-161.
(30) Afeworki, M.; McKay, R. A.; Schaefer, J. *Macromolecules* 1992, 25, 4084-4091.
(31) Rosay, M.; Weis, V.; Kreischer, K. E.; Temkin, R. J.; Griffin, R. G. *J. Am. Chem. Soc.* 2002, 124, 3214-3215.
(32) Bajaj, V. S.; Farrar, C. T.; Mastovsky, I.; Vieregg, J.; Bryant, J.; Elena, B.; Kreischer, K. E.; Temkin, R. J.; Griffin, R. G. *J. Magn. Reson.* 2003, 160, 85-90.
(33) Goldman, M. *Spin Temperature and Nuclear Magnetic Resonance in Solids*; Clarendon Press: Oxford, 1970.
(34) Hwang, C. F.; Hill, D. A. *Phys. Rev. Lett.* 1967, 19, 1011-1014.
(35) Hwang, C. F.; Hill, D. A. *Phys. Rev. Lett.* 1967, 18, 110-112.
(36) Kessenikh, A. V.; Lushchikov, V. I.; Manenkov, A. A.; Taran, Y. V. *Soviet Physics-Solid State* 1963, 5, 321-329.
(37) Kessenikh, A. V.; Manenkov, A. A.; Pyatnitskii, G. I. *Soviet Physics-Solid State* 1964, 6, 641-643.
(38) Wollan, D. S. *Physical Review B* 1976, 13, 3686-3696.
(39) Wollan, D. S. *Physical Review B* 1976, 13, 3671-3685.
(40) Atsarkin, V. A. *Sov. Phys. Usp.* 1978, 21, 725-744.
(41) Luckhurst, G. R., Biradicals as Spin Probes. In *Spin Labeling Theory and Applications*, Berliner, L. J., Ed. Academic Press: New York, 1976; pp 133-181.
(42) Atherton, N. M. *Principles of Electron Spin Resonance*; Ellis Horwood: PTR Prentice Hall, 1993.
(43) Bennett, A. E.; Rienstra, C. M.; Auger, M.; Lakshmi, K. V.; Griffin, R. G. *J. Chem. Phys.* 1995, 103, 6951-6958.
(44) Bajaj, V. S.; Mak, M.; Hornstein, M. K.; Belenky, M.; Herzfeld, J.; Temkin, R. J.; Griffin, R. G. *Biophys. J.* 2005, 88, 203A-203A.

(45) Mak, M. L.; Bajaj, V. S.; Hornstein, M. K.; Belenky, M.; Temkin, R. J.; Griffin, R. G.; Herzfeld, J. *Biophys. J.* 2005, 88, 506A-506A.
(46) Nelson, R.; Sawaya, M. R.; Balbimie, M.; Madsen, A. O.; Riekel, C.; Grothe, R.; Eisenberg, D. *Nature* 2005, 435, 773-778.
(47) Van Der Wel, P.; Hu, K.-N.; Lewandowski, J.; Griffin, R. G. *in preparation*.
(48) Martin, R. W.; Zilm, K. W. *J. Magn. Reson.* 2003, 165, 162-174.
(49) Igumenova, T. I.; McDermott, A. E.; Zilm, K. W.; Martin, R. W.; Paulson, E. K.; Wand, A. J. *J. Am. Chem. Soc.* 2004, 126, 6720-6727.
(50) Franks, W. T.; Zhou, D. H.; Wylie, B. J.; Money, B. G.; Graesser, D. T.; Frericks, H. L.; Sahota, G.; Rienstra, C. M. *J. Am. Chem. Soc.* 2005, 127, 12291-12305.

What is claimed is:

1. A method comprising steps of:
providing a frozen sample in a magnetic field, wherein the sample includes a biradical and an analyte with at least one spin half nucleus;
polarizing the at least one spin half nucleus of the analyte by irradiating the frozen sample with radiation having a frequency that excites electron spin transitions in the biradical;
optionally melting the frozen sample to produce a molten sample; and
detecting nuclear spin transitions in the at least one spin half nucleus of the analyte in the frozen or molten sample, wherein the biradical has the formula (I):

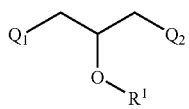

(I)

wherein
$Q_1$ is a cyclic nitroxide group of the formula:

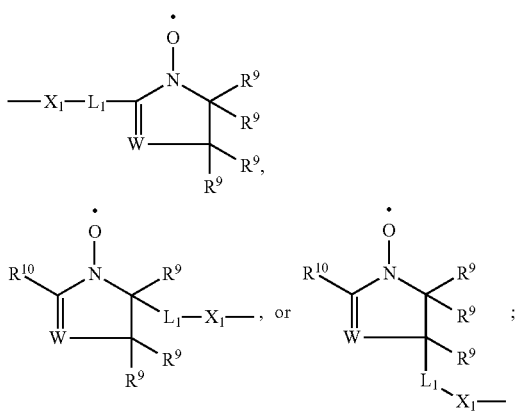

wherein each instance of $R^9$ is, independently, hydrogen, substituted or unsubstituted hydroxyl; substituted or unsubstituted thiol; substituted or unsubstituted amino; nitro; halo; cyano; azido; substituted or unsubstituted, cyclic or acyclic $C_{1-6}$ aliphatic; substituted or unsubstituted, cyclic or acyclic $C_{1-6}$ heteroaliphatic; substituted or unsubstituted aryl, substituted or unsubstituted heteroaryl; acyl; $C_{1-6}$ alkyl sulfonyl; $C_{1-6}$ alkyl sulfinyl; substituted or unsubstituted aryl sulfinyl; or substituted or unsubstituted aryl sulfonyl;

$R^{10}$ is hydrogen, substituted or unsubstituted, cyclic or acyclic $C_{1-6}$ aliphatic; substituted or unsubstituted, cyclic or acyclic $C_{1-6}$ heteroaliphatic; substituted or unsubstituted aryl, or substituted or unsubstituted heteroaryl;

W is N or $\oplus$ N—O$\ominus$;

$Q_2$ is the group —$X_2$-$L_2$-$M_2$, where $Q_1$ and $Q_2$ may be the same or different;

$R^1$ is hydrogen; a suitable hydroxyl protecting group; substituted or unsubstituted, cyclic or acyclic $C_{1-6}$ aliphatic; substituted or unsubstituted, cyclic or acyclic $C_{1-6}$ heteroaliphatic; substituted or unsubstituted aryl, substituted or unsubstituted heteroaryl; acyl; $C_{1-6}$ alkyl sulfonyl; $C_{1-6}$ alkyl sulfinyl; substituted or unsubstituted aryl sulfinyl; or substituted or unsubstituted aryl sulfonyl;

$X_1$ and $X_2$ are, independently, —O—, —S—, or —N($R^2$)—, wherein $R^2$ is hydrogen, a suitable amino protecting group; substituted or unsubstituted amino; substituted or unsubstituted hydroxyl; substituted or unsubstituted, cyclic or acyclic $C_{1-6}$ aliphatic; substituted or unsubstituted, cyclic or acyclic $C_{1-6}$ heteroaliphatic; substituted or unsubstituted aryl; substituted or unsubstituted heteroaryl; acyl; $C_{1-6}$ alkyl sulfonyl; $C_{1-6}$ alkyl sulfinyl; substituted or unsubstituted aryl sulfinyl; or substituted or unsubstituted aryl sulfonyl;

$L_1$ and $L_2$ are, independently, a direct bond; substituted or unsubstituted, cyclic or acyclic $C_{1-6}$ aliphatic; or substituted or unsubstituted, cyclic or acyclic $C_{1-6}$ heteroaliphatic; and $M_2$ is a substituted or unsubstituted, cyclic or acyclic nitroxide.

2. The method of claim 1 with the proviso that $Q_1$ and $Q_2$ are different when $X_1$ and $X_2$ are —O—.

3. The method of claim 1, wherein $M_2$ is a cyclic or acyclic nitroxide of the formula:

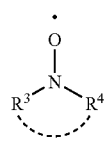

wherein $R^3$ and $R^4$ are, independently, substituted or unsubstituted, cyclic or acyclic aliphatic; substituted or unsubstituted, cyclic or acyclic heteroaliphatic; substituted or unsubstituted aryl; substituted or unsubstituted heteroaryl; wherein is a group which optionally joins $R^3$ and $R^4$ to form a 5- to 6-membered heterocyclic ring, and with the proviso that each group $R^3$ or $R^4$ does not contain hydrogens alpha to the (N—O·) group;

and
$Q_2$ corresponds to the formula:

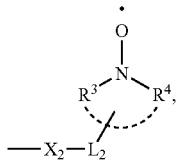

wherein the point of attachment of the group $L_2$-$X_2$ is to either $R^3$, to $R^4$, or to the 5- to 6-membered heterocyclic ring formed by the joining of $R^3$ and $R^4$.

4. The method of claim 1, wherein $Q_2$ is a cyclic nitroxide group of the formula:

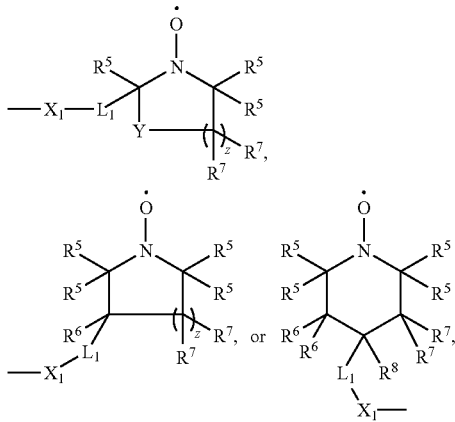

wherein each instance of $R^5$ is, independently, substituted or unsubstituted, cyclic or acyclic $C_{1-6}$ aliphatic; substituted or unsubstituted, cyclic or acyclic $C_{1-6}$ heteroaliphatic; substituted or unsubstituted aryl, substituted or unsubstituted heteroaryl, with the proviso that each group $R^5$ does not contain hydrogens alpha to the (N—O.) group;

Y is —O—, —S—, —N($R^2$)—, or —C($R^6$)$_2$—;

$R^2$ is hydrogen, a suitable amino protecting group; substituted or unsubstituted amino; substituted or unsubstituted hydroxyl; substituted or unsubstituted, cyclic or acyclic $C_{1-6}$ aliphatic; substituted or unsubstituted, cyclic or acyclic $C_{1-6}$ heteroaliphatic; substituted or unsubstituted aryl, substituted or unsubstituted heteroaryl, acyl; $C_{1-6}$ alkyl sulfonyl; $C_{1-6}$ alkyl sulfinyl; substituted or unsubstituted aryl sulfinyl; or substituted or unsubstituted aryl sulfonyl;

each $R^6$, $R^7$, and $R^8$ is, independently hydrogen, substituted or unsubstituted hydroxyl; substituted or unsubstituted thiol; substituted or unsubstituted amino; nitro; halo; cyano; azido; substituted or unsubstituted, cyclic or acyclic $C_{1-6}$ aliphatic; substituted or unsubstituted, cyclic or acyclic $C_{1-6}$ heteroaliphatic; substituted or unsubstituted aryl, substituted or unsubstituted heteroaryl, acyl; $C_{1-6}$ alkyl sulfonyl; $C_{1-6}$ alkyl sulfinyl; substituted or unsubstituted aryl sulfinyl; or substituted or unsubstituted aryl sulfonyl; and z is 1 or 2.

5. The method of claim 1, wherein $Q_2$ is a cyclic nitroxide group of the formula:

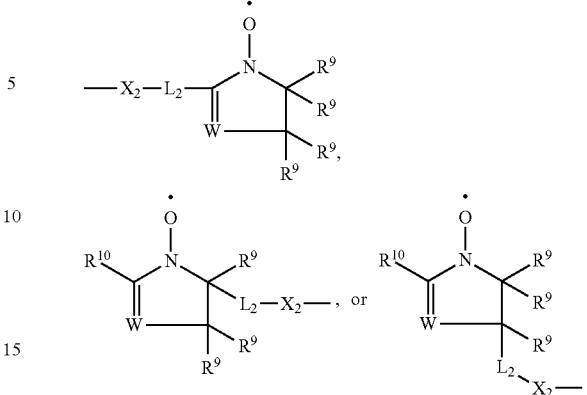

wherein each instance of $R^9$ is, independently, hydrogen, substituted or unsubstituted hydroxyl; substituted or unsubstituted thiol; substituted or unsubstituted amino; nitro; halo; cyano; azido; substituted or unsubstituted, cyclic or acyclic $C_{1-6}$ aliphatic; substituted or unsubstituted, cyclic or acyclic $C_{1-6}$ heteroaliphatic; substituted or unsubstituted aryl, substituted or unsubstituted heteroaryl, acyl; $C_{1-6}$ alkyl sulfonyl; $C_{1-6}$ alkyl sulfinyl; substituted or unsubstituted aryl sulfinyl; or substituted or unsubstituted aryl sulfonyl;

$R^{10}$ is hydrogen, substituted or unsubstituted, cyclic or acyclic $C_{1-6}$ aliphatic; substituted or unsubstituted, cyclic or acyclic $C_{1-6}$ heteroaliphatic; substituted or unsubstituted aryl, or substituted or unsubstituted heteroaryl; and W is N or $\oplus$N—O$\ominus$.

6. The method of claim 1, wherein $L_1$ and $L_2$ are independently, a single bond or —CH$_2$—.

7. The method of claim 1, further comprising a step of:
freezing a sample within a magnetic field to provide the frozen sample in a magnetic field.

8. The method of claim 1, wherein the method does not include a step of melting the sample to produce a molten sample and, in the step of detecting, the nuclear spin transitions in the at least one spin half nucleus of the analyte in the frozen sample are detected by solid-state NMR.

9. The method of claim 1, wherein the method does include a step of melting the sample to produce a molten sample and, in the step of detecting, the nuclear spin transitions in the at least one spin half nucleus of the analyte in the molten sample are detected by liquid-state NMR.

10. The method of claim 9, wherein the analyte is a protein or nucleic acid.

11. The method of claim 9, wherein the analyte is a metabolite.

12. The method of claim 11, wherein the metabolite is present in the sample at a concentration of less than 1 µM.

13. The method of claim 9, further comprising a step of:
freezing a sample in a magnetic field to provide the frozen sample in a magnetic field.

14. The method of claim 13, further comprising repeating the freezing, polarizing, melting and detecting steps at least once.

15. The method of claim 14, wherein in the step of freezing, the sample is cooled to a temperature of less than about 200 K.

16. The method of claim 14, wherein in the step of freezing, the sample is cooled to a temperature in the range of about 1 K to about 100 K.

17. The method of claim 14, wherein in the step of freezing, the sample is cooled to a temperature of about 90 K.

18. The method of claim 14, wherein the step of freezing is completed in less than about 2 minutes.

19. The method of claim 14, wherein the step of freezing is completed in less than about 1 minute.

20. The method of claim 1, wherein the method does include a step of melting the sample to produce a molten sample and, in the step of detecting, the nuclear spin transitions in the at least one spin half nucleus of the analyte in the molten sample are detected by MRI.

21. The method of claim 20, wherein the spin half nucleus of the analyte has a $T_1$ relaxation time of at least 6 seconds at 310 K in $D_2O$ in a magnetic field of 7 T.

22. The method of claim 21 further comprising a step of administering at least a portion of the molten sample that includes the analyte to a subject before the step of detecting.

23. The method of claim 1, wherein the at least one spin half nucleus has a γ-value smaller than that of $^1H$ and the step of polarizing further comprises irradiating the frozen sample with radiation having a frequency that causes cross-polarization between a $^1H$ nucleus present in the sample and the at least one spin half nucleus of the analyte.

24. The method of claim 23, wherein the at least one spin half nucleus is a $^{13}C$ nucleus.

25. The method of claim 23, wherein the at least one spin half nucleus is a $^{15}N$ nucleus.

26. The method of claim 23, wherein the at least one spin half nucleus is a $^{19}F$ nucleus.

27. The method of claim 23, wherein the $^1H$ nucleus present in the sample is from $^1H_2O$.

28. The method of claim 1, wherein the at least one spin half nucleus is a $^1H$ nucleus.

29. The method of claim 1, wherein in the optional step of melting, the frozen sample is exposed to radiation having a wavelength of less than about 100 μm.

30. The method of claim 29, wherein in the optional step of melting, the frozen sample is exposed to radiation having a wavelength in the range of about 0.5 μm and about 50 μm.

31. The method of claim 29, wherein the radiation is from a laser.

32. The method of claim 31, wherein the laser is a $CO_2$ laser.

33. The method of claim 29, wherein the radiation is from a lamp.

34. The method of claim 29, wherein in the optional step of melting, the frozen sample is exposed to the radiation using an optical fiber.

35. The method of claim 29, wherein in the optional step of melting, the frozen sample is within a cylindrical rotor.

36. The method of claim 35, wherein the cylindrical rotor is made of quartz.

37. The method of claim 35, wherein the cylindrical rotor is spun during at least the step of melting.

38. The method of claim 1, wherein the optional step of melting is completed in less than about 1 second.

39. The method of claim 1, wherein the magnetic field has a strength in the range of about 0.1 T to about 30 T.

40. The method of claim 39, wherein the radiation has a frequency in the range of about 2.8 GHz to about 840 GHz.

41. The method of claim 40, wherein the radiation has a frequency of about 140 GHz.

42. The method of claim 1, wherein the magnetic field has a strength of about 5 T.

43. A method comprising steps of:

providing a frozen sample in a magnetic field, wherein the sample includes a biradical and an analyte with at least one spin half nucleus;

polarizing the at least one spin half nucleus of the analyte by irradiating the frozen sample with radiation having a frequency that excites electron spin transitions in the biradical;

optionally melting the frozen sample to produce a molten sample; and detecting nuclear spin transitions in the at least one spin half nucleus of the analyte in the frozen or molten sample, wherein the biradical has the formula (I):

(I)

wherein $Q_1$ is the group —$X_1$—$L_1$—$M_1$;

$Q_2$ is the group —$X_2$—$L_2$—$M_2$, where $Q_1$ and $Q_2$ may be the same or different;

$R^1$ is hydrogen; a suitable hydroxyl protecting group; substituted or unsubstituted, cyclic or acyclic $C_{1-6}$ aliphatic; substituted or unsubstituted, cyclic or acyclic $C_{1-6}$ heteroaliphatic; substituted or unsubstituted aryl, substituted or unsubstituted heteroaryl; acyl; $C_{1-6}$ alkyl sulfonyl; $C_{1-6}$ alkyl sulfinyl; substituted or unsubstituted aryl sulfinyl; or substituted or unsubstituted aryl sulfonyl;

$X_1$ is —O—, and $X_2$ is —$N(R^2)$—, wherein $R^2$ is hydrogen, a suitable amino protecting group; substituted or unsubstituted amino; substituted or unsubstituted hydroxyl; substituted or unsubstituted, cyclic or acyclic $C_{1-6}$ aliphatic; substituted or unsubstituted, cyclic or acyclic $C_{1-6}$ heteroaliphatic; substituted or unsubstituted aryl; substituted or unsubstituted heteroaryl; acyl; $C_{1-6}$ alkyl sulfonyl; $C_{1-6}$ alkyl sulfinyl; substituted or unsubstituted aryl sulfinyl; or substituted or unsubstituted aryl sulfonyl;

$L_1$ and $L_2$ are independently a direct bond; substituted or unsubstituted, cyclic or acyclic $C_{1-6}$ aliphatic; or substituted or unsubstituted, cyclic or acyclic $C_{1-6}$ heteroaliphatic; and $M_1$ and $M_2$ are, independently, a substituted or unsubstituted, cyclic or acyclic nitroxide.

44. The method of claim 43, wherein $R^2$ is hydrogen.

45. A method comprising steps of:

providing a frozen sample in a magnetic field, wherein the sample includes a biradical and an analyte with at least one spin half nucleus;

polarizing the at least one spin half nucleus of the analyte by irradiating the frozen sample with radiation having a frequency that excites electron spin transitions in the biradical;

optionally melting the frozen sample to produce a molten sample; and detecting nuclear spin transitions in the at least one spin half nucleus of the analyte in the frozen or molten sample, wherein the biradical has the formula (IIA):

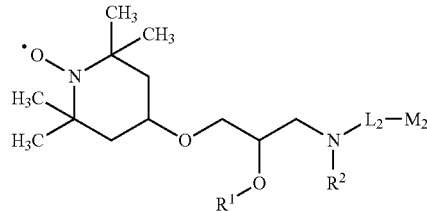
(IIA)

wherein
R¹ is hydrogen; a suitable hydroxyl protecting group; substituted or unsubstituted, cyclic or acyclic $C_{1-6}$ aliphatic; substituted or unsubstituted, cyclic or acyclic $C_{1-6}$ heteroaliphatic; substituted or unsubstituted aryl, substituted or unsubstituted heteroaryl; acyl; $C_{1-6}$ alkyl sulfonyl; $C_{1-6}$ alkyl sulfinyl; substituted or unsubstituted aryl sulfinyl; or substituted or unsubstituted aryl sulfonyl;

R² is hydrogen, a suitable amino protecting group; substituted or unsubstituted amino; substituted or unsubstituted hydroxyl; substituted or unsubstituted, cyclic or acyclic $C_{1-6}$ aliphatic; substituted or unsubstituted, cyclic or acyclic $C_{1-6}$ heteroaliphatic; substituted or unsubstituted aryl; substituted or unsubstituted heteroaryl; acyl; $C_{1-6}$ alkyl sulfonyl; $C_{1-6}$ alkyl sulfinyl; substituted or unsubstituted aryl sulfinyl; or substituted or unsubstituted aryl sulfonyl;

L₂ is a direct bond; substituted or unsubstituted, cyclic or acyclic $C_{1-6}$ aliphatic; or substituted or unsubstituted, cyclic or acyclic $C_{1-6}$ heteroaliphatic; and M₂ is a substituted or unsubstituted, cyclic or acyclic nitroxide.

46. The method of claim 45, wherein the biradical is a biradical of formula:

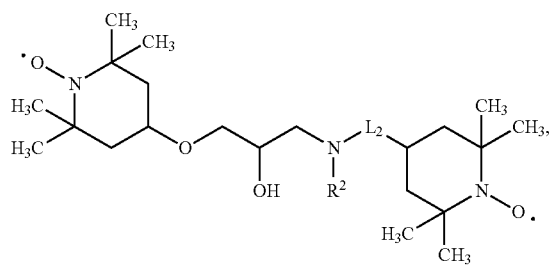
(IIB)

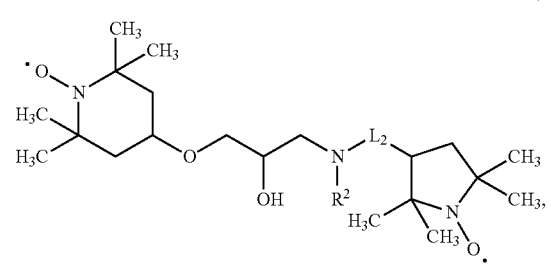
(IIC)

-continued

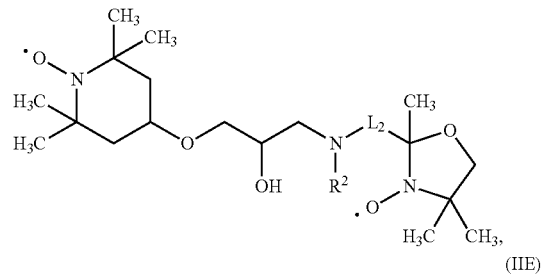
(IID)

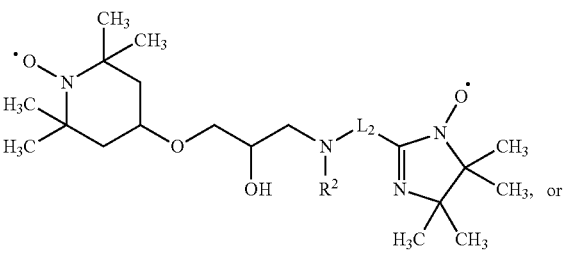
(IIE)

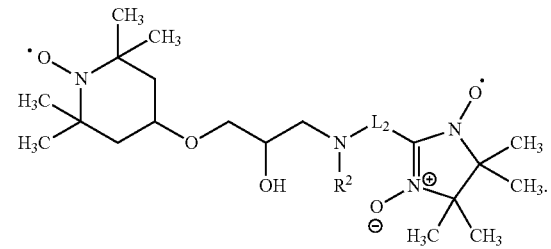
(IIF)

47. The method of claim 45, wherein the biradical is 1-(TEMPO-4-oxy)-3-(TEMPO-4-amino)-propan-2-ol.

48. A biradical having the structure of formula (I):

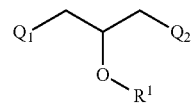
(I)

wherein

Q₁ is a cyclic nitroxide group of the formula:

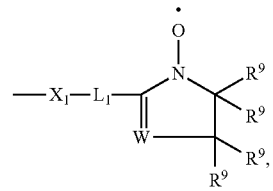

-continued

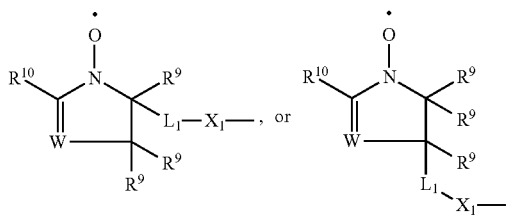

wherein each instance of $R^9$ is, independently, hydrogen, substituted or unsubstituted hydroxyl; substituted or unsubstituted thiol; substituted or unsubstituted amino; nitro; halo; cyano; azido; substituted or unsubstituted, cyclic or acyclic $C_{1-6}$ aliphatic; substituted or unsubstituted, cyclic or acyclic $C_{1-6}$ heteroaliphatic; substituted or unsubstituted aryl, substituted or unsubstituted heteroaryl, acyl; $C_{1-6}$ alkyl sulfonyl; $C_{1-6}$ alkyl sulfinyl; substituted or unsubstituted aryl sulfinyl; or substituted or unsubstituted aryl sulfonyl;

$R^{10}$ is hydrogen, substituted or unsubstituted, cyclic or acyclic $C_{1-6}$ aliphatic; substituted or unsubstituted, cyclic or acyclic $C_{1-6}$ heteroaliphatic; substituted or unsubstituted aryl, or substituted or unsubstituted heteroaryl;

W is N or $\oplus$N—O$\ominus$;

$Q_2$ is the group —$X_2$-$L_2$-$M_2$, where $Q_1$ and $Q_2$ may be the same or different;

$R'$ is hydrogen; a suitable hydroxyl protecting group; substituted or unsubstituted, cyclic or acyclic $C_{1-6}$ aliphatic; substituted or unsubstituted, cyclic or acyclic $C_{1-6}$ heteroaliphatic; substituted or unsubstituted aryl, substituted or unsubstituted heteroaryl; acyl; $C_{1-6}$ alkyl sulfonyl; $C_{1-6}$ alkyl sulfinyl; substituted or unsubstituted aryl sulfinyl; or substituted or unsubstituted aryl sulfonyl;

$X_1$ and $X_2$ are, independently, —O—, —S—, or —N($R^2$)—, wherein $R^2$ is hydrogen, a suitable amino protecting group; substituted or unsubstituted amino; substituted or unsubstituted hydroxyl; substituted or unsubstituted, cyclic or acyclic $C_{1-6}$ aliphatic; substituted or unsubstituted, cyclic or acyclic $C_{1-6}$ heteroaliphatic; substituted or unsubstituted aryl; substituted or unsubstituted heteroaryl; acyl; $C_{1-6}$ alkyl sulfonyl; $C_{1-6}$ alkyl sulfinyl; substituted or unsubstituted aryl sulfinyl; or substituted or unsubstituted aryl sulfonyl, with the proviso that $Q_1$ and $Q_2$ are different when $X_1$ and $X_2$ are —O—;

$L_1$ and $L_2$ are, independently, a direct bond; substituted or unsubstituted, cyclic or acyclic $C_{1-6}$ aliphatic; or substituted or unsubstituted, cyclic or acyclic $C_{1-6}$ heteroaliphatic; and $M_2$ is a substituted or unsubstituted, cyclic or acyclic nitroxide.

49. The biradical of claim 48, wherein $M_2$ is a cyclic or acyclic nitroxide of the formula:

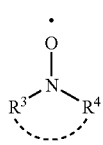

wherein $R^3$ and $R^4$ are, independently, substituted or unsubstituted, cyclic or acyclic aliphatic; substituted or unsubstituted, cyclic or acyclic heteroaliphatic; substituted or unsubstituted aryl; substituted or unsubstituted heteroaryl; wherein

is a group which optionally joins $R^3$ and $R^4$ to form a 5- to 6-membered heterocyclic ring, and with the proviso that each group $R^3$ or $R^4$ does not contain hydrogens alpha to the (N—O.) group;
and $Q_2$ corresponds to the formula:

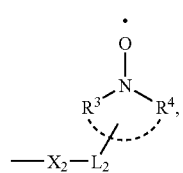

wherein the point of attachment of the group $L_2$-$X_2$ is to either $R^3$, to $R^4$, or to the 5- to 6-membered heterocyclic ring formed by the joining of $R^3$ and $R^4$.

50. The biradical of claim 48, wherein $Q_2$ is a cyclic nitroxide group of the formula:

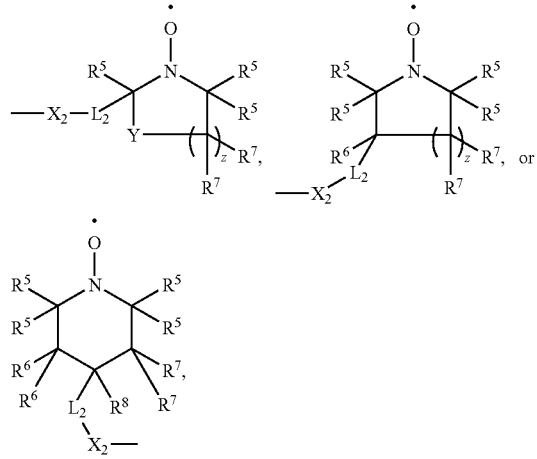

wherein each instance of $R^5$ is, independently, substituted or unsubstituted, cyclic or acyclic $C_{1-6}$ aliphatic; substituted or unsubstituted, cyclic or acyclic $C_{1-6}$ heteroaliphatic; substituted or unsubstituted aryl, substituted or unsubstituted heteroaryl, with the proviso that each group $R^5$ does not contain hydrogens alpha to the (N—O·) group;

Y is —O—, —S—, —N($R^2$)—, or —C($R^6$)$_2$—;

$R^2$ is hydrogen, a suitable amino protecting group; substituted or unsubstituted amino; substituted or unsubstituted hydroxyl; substituted or unsubstituted, cyclic or acyclic $C_{1-6}$ aliphatic; substituted or unsubstituted, cyclic or acyclic $C_{1-6}$ heteroaliphatic; substituted or unsubstituted aryl, substituted or unsubstituted heteroaryl; acyl; $C_{1-6}$ alkyl sulfonyl; $C_{1-6}$ alkyl sulfinyl; substituted or unsubstituted aryl sulfinyl; or substituted or unsubstituted aryl sulfonyl;

each $R^6$, $R^7$, and $R^8$ is, independently hydrogen, substituted or unsubstituted hydroxyl; substituted or unsubstituted thiol; substituted or unsubstituted amino; nitro; halo; cyano; azido; substituted or unsubstituted, cyclic or acyclic $C_{1-6}$ aliphatic; substituted or unsubstituted, cyclic or acyclic $C_{1-6}$ heteroaliphatic; substituted or unsubstituted aryl, substituted or unsubstituted heteroaryl, acyl; $C_{1-6}$ alkyl sulfonyl; $C_{1-6}$ alkyl sulfinyl; substituted or unsubstituted aryl sulfinyl; or substituted or unsubstituted aryl sulfonyl; and z is 1 or 2.

51. The biradical of claim 48, wherein $Q_2$ is a cyclic nitroxide group of the formula:

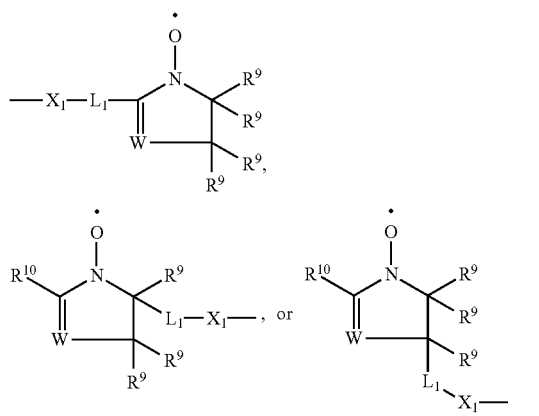

wherein each instance of $R^9$ is, independently, hydrogen, substituted or unsubstituted hydroxyl; substituted or unsubstituted thiol; substituted or unsubstituted amino; nitro; halo; cyano; azido; substituted or unsubstituted, cyclic or acyclic $C_{1-6}$ aliphatic; substituted or unsubstituted, cyclic or acyclic $C_{1-6}$ heteroaliphatic; substituted or unsubstituted aryl, substituted or unsubstituted heteroaryl, acyl; $C_{1-6}$ alkyl sulfonyl; $C_{1-6}$ alkyl sulfinyl; substituted or unsubstituted aryl sulfinyl; or substituted or unsubstituted aryl sulfonyl;

$R^{10}$ is hydrogen, substituted or unsubstituted, cyclic or acyclic $C_{1-6}$ aliphatic; substituted or unsubstituted, cyclic or acyclic $C_{1-6}$ heteroaliphatic; substituted or unsubstituted aryl, or substituted or unsubstituted heteroaryl; and W is N or $\oplus$N—O$\ominus$.

52. The biradical of claim 48, wherein $L_1$ and $L_2$ are independently, a single bond or —CH$_2$—.

53. A biradical having the structure of formula (I):

wherein $Q_1$ is the group —$X_1$—$L_1$—$M_1$;

$Q_2$ is the group —$X_2$—$L_2$—$M_2$, where $Q_1$ and $Q_2$ may be the same or different;

$R^1$ is hydrogen; a suitable hydroxyl protecting group; substituted or unsubstituted, cyclic or acyclic $C_{1-6}$ aliphatic; substituted or unsubstituted, cyclic or acyclic $C_{1-6}$ heteroaliphatic; substituted or unsubstituted aryl, substituted or unsubstituted heteroaryl; acyl; $C_{1-6}$ alkyl sulfonyl; $C_{1-6}$ alkyl sulfinyl; substituted or unsubstituted aryl sulfinyl; or substituted or unsubstituted aryl sulfonyl;

$X_1$ is —O—, and $X_2$ is —N($R^2$)—, wherein $R^2$ is hydrogen, a suitable amino protecting group; substituted or unsubstituted amino; substituted or unsubstituted hydroxyl; substituted or unsubstituted, cyclic or acyclic $C_{1-6}$ aliphatic; substituted or unsubstituted, cyclic or acyclic $C_{1-6}$ heteroaliphatic; substituted or unsubstituted aryl; substituted or unsubstituted heteroaryl; acyl; $C_{1-6}$ alkyl sulfonyl; $C_{1-6}$ alkyl sulfinyl; substituted or unsubstituted aryl sulfinyl; or substituted or unsubstituted aryl sulfonyl, with the proviso that $Q_1$ and $Q_2$, are different when $X_1$ and $X_2$ are —O—;

$L_1$ and $L_2$ are independently a direct bond; substituted or unsubstituted, cyclic or acyclic $C_{1-6}$ aliphatic; or substituted or unsubstituted, cyclic or acyclic $C_{1-6}$ heteroaliphatic; and $M_1$ and $M_2$ are, independently, a substituted or unsubstituted, cyclic or acyclic nitroxide.

54. The biradical of claim 53, wherein $R^2$ is hydrogen.

55. A biradical having the structure of formula (IIA):

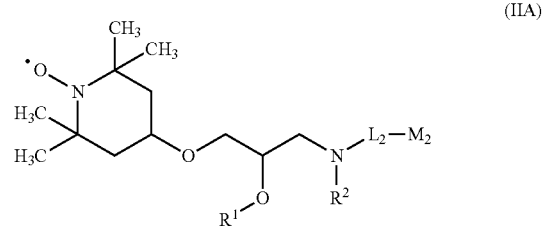

wherein $R^1$ is hydrogen; a suitable hydroxyl protecting group; substituted or unsubstituted, cyclic or acyclic $C_{1-6}$ aliphatic; substituted or unsubstituted, cyclic or acyclic $C_{1-6}$ heteroaliphatic; substituted or unsubstituted aryl, substituted or unsubstituted heteroaryl; acyl; $C_{1-6}$ alkyl sulfonyl; $C_{1-6}$ alkyl sulfinyl; substituted or unsubstituted aryl sulfinyl; or substituted or unsubstituted aryl sulfonyl;

$R^2$ is hydrogen, a suitable amino protecting group; substituted or unsubstituted amino; substituted or unsubstituted hydroxyl; substituted or unsubstituted, cyclic or acyclic $C_{1-6}$ aliphatic; substituted or unsubstituted, cyclic or acyclic $C_{1-6}$ heteroaliphatic; substituted or unsubstituted aryl; substituted or unsubstituted heteroaryl; acyl; $C_{1-6}$ alkyl sulfonyl; $C_{1-6}$ alkyl sulfinyl; substituted or unsubstituted aryl sulfinyl; or substituted or unsubstituted aryl sulfonyl, with the proviso that $Q_1$ and $Q_2$ are different when $X_1$ and $X_2$ are —O—;

$L_2$ is a direct bond; substituted or unsubstituted, cyclic or acyclic $C_{1-6}$ aliphatic; or substituted or unsubstituted, cyclic or acyclic $C_{1-6}$ heteroaliphatic; and $M_2$ is a substituted or unsubstituted, cyclic or acyclic nitroxide.

56. The biradical of claim 55, wherein the biradical is a biradical of formula:

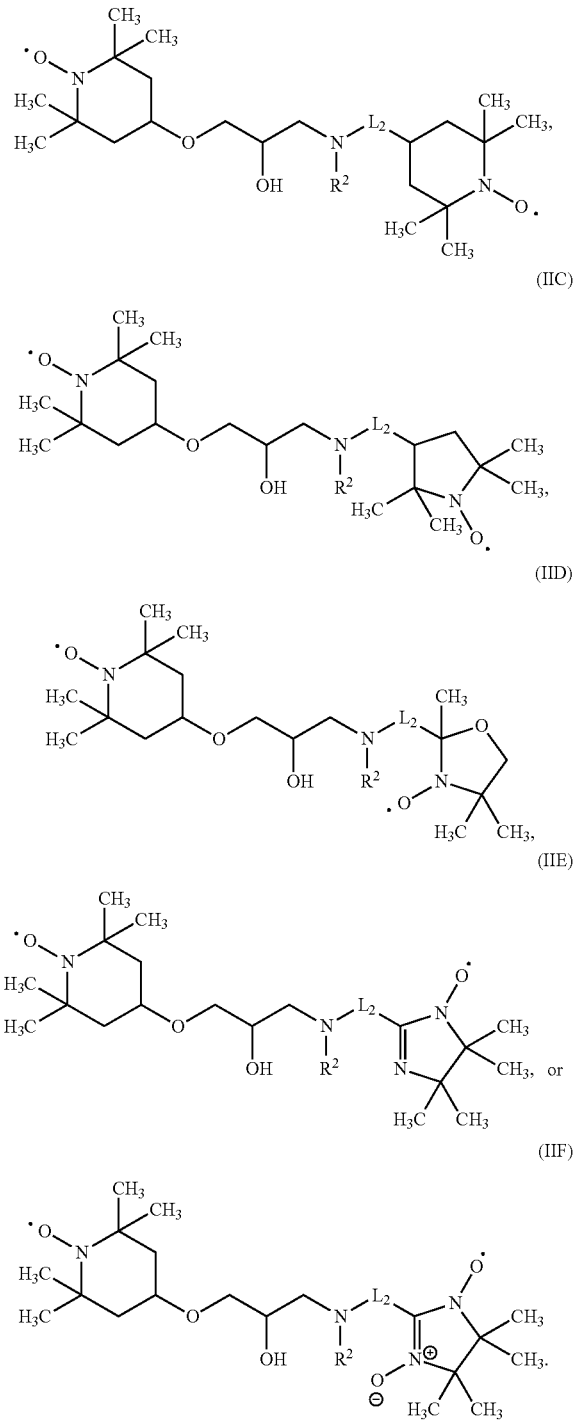

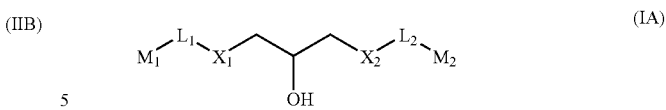

wherein $X_1$ and $X_2$ are independently, —O—, —S—, or —N($R^2$)—, wherein $R^2$ is hydrogen, a suitable amino protecting group; substituted or unsubstituted amino; substituted or unsubstituted hydroxyl; substituted or unsubstituted, cyclic or acyclic $C_{1-6}$ aliphatic; substituted or unsubstituted; cyclic or acyclic $C_{1-6}$ heteroaliphatic; substituted or unsubstituted aryl, substituted or unsubstituted heteroaryl, acyl; $C_{1-6}$ alkyl sulfonyl; $C_{1-6}$ alkyl sulfinyl; substituted or unsubstituted aryl sulfinyl; or substituted or unsubstituted aryl sulfonyl;

$L_1$ and $L_2$ are, independently, a direct bond; substituted or unsubstituted, cyclic or acyclic $C_{1-6}$ aliphatic; or substituted or unsubstituted, cyclic or acyclic $C_{1-6}$ heteroaliphatic; and $M_1$ and $M_2$ are, independently, a substituted or unsubstituted, cyclic or acyclic nitroxide; the method comprising steps of:

(i) reacting a compound of formula:

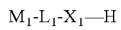

with a compound of formula:

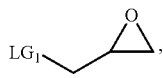

wherein $LG_1$ is a suitable leaving group, to provide a compound of formula:

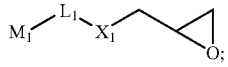

and then (ii) reacting the compound of formula:

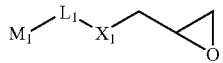

with a compound of formula:

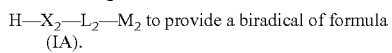

59. The method of claim 58, wherein $LG_1$ is —I, —Br, or —Cl.

60. The method of claim 58, wherein $LG_1$ is —Cl.

61. The method of claim 58, wherein $X_1$ is —O—.

62. The method of claim 58, wherein $X_2$ is —NH—.

63. The method of claim 58, wherein the biradical is 1-(TEMPO-4-oxy)-3-(TEMPO-4-amino)-propan-2-ol.

57. The biradical of claim 55, wherein the biradical is 1-(TEMPO-4-oxy)-3-(TEMPO-4-amino)-propan-2-ol.

58. A method of making a biradical having the formula (IA):

* * * * *